(12) United States Patent
Jia et al.

(10) Patent No.: US 10,588,572 B2
(45) Date of Patent: Mar. 17, 2020

(54) BULK MOTION SUBTRACTION IN OPTICAL COHERENCE TOMOGRAPHY ANGIOGRAPHY

(71) Applicant: Oregon Health & Science University, Portland, OR (US)

(72) Inventors: Yali Jia, Portland, OR (US); David Huang, Portland, OR (US); Yan Li, Portland, OR (US); Acner Camino, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 258 days.

(21) Appl. No.: 15/805,392

(22) Filed: Nov. 7, 2017

(65) Prior Publication Data
US 2018/0317851 A1    Nov. 8, 2018

Related U.S. Application Data

(60) Provisional application No. 62/503,306, filed on May 8, 2017.

(51) Int. Cl.
*G06K 9/00* (2006.01)
*A61B 5/00* (2006.01)
(Continued)

(52) U.S. Cl.
CPC ........... *A61B 5/7207* (2013.01); *A61B 3/102* (2013.01); *A61B 5/0066* (2013.01); *A61B 5/0261* (2013.01); *A61B 5/7235* (2013.01); *G06T 5/002* (2013.01); *G06T 7/11* (2017.01); *G06T 7/136* (2017.01); *G06T 7/194* (2017.01);
(Continued)

(58) Field of Classification Search
None
See application file for complete search history.

(56) References Cited

U.S. PATENT DOCUMENTS 8,223,143 B2 *  7/2012  Dastmalchi ............ A61B 3/102
                                                    345/418
10,165,941 B2 *  1/2019  Walsh ..................... A61B 3/102
(Continued)

*Primary Examiner* — Atiba O Fitzpatrick
(74) *Attorney, Agent, or Firm* — Schwabe, Williamson & Wyatt, P.C.

(57) ABSTRACT

Described herein is an algorithm to remove decorrelation noise due to bulk motion in optical coherence tomography angiography (OCTA). OCTA B-frames are divided into segments within which the bulk motion velocity could be assumed constant. This velocity is recovered using linear regression of decorrelation versus the logarithm of reflectance in axial lines (A-lines) identified as bulk tissue by percentile analysis. The fitting parameters are used to calculate a reflectance-adjusted threshold for bulk motion decorrelation. Below this threshold, voxels are identified as non-flow tissue, and their flow values are set to zeros. Above this threshold, the voxels are identified as flow voxels and bulk motion velocity is subtracted from each using a non-linear decorrelation-velocity relationship. Compared to the median-subtraction method, the bulk motion subtraction algorithm described herein improves angiogram signal-to-noise ratio, contrast, vessel density repeatability, and bulk motion noise cleanup, while preserving the connectivity of the vascular networks in the angiogram.

24 Claims, 17 Drawing Sheets

(51) Int. Cl.
*A61B 5/026* (2006.01)
*G06T 7/194* (2017.01)
*A61B 3/10* (2006.01)
*G06T 5/00* (2006.01)
*G06T 7/136* (2017.01)
*G06T 7/11* (2017.01)

(52) U.S. Cl.
CPC ......... *A61B 5/7275* (2013.01); *A61B 2576/02* (2013.01); *G06T 2207/10101* (2013.01); *G06T 2207/30041* (2013.01)

(56) References Cited

U.S. PATENT DOCUMENTS

2013/0141695 A1* 6/2013 Buckland ............... A61B 3/102
 351/206
2018/0122077 A1* 5/2018 Wada ...................... G06T 7/248

\* cited by examiner

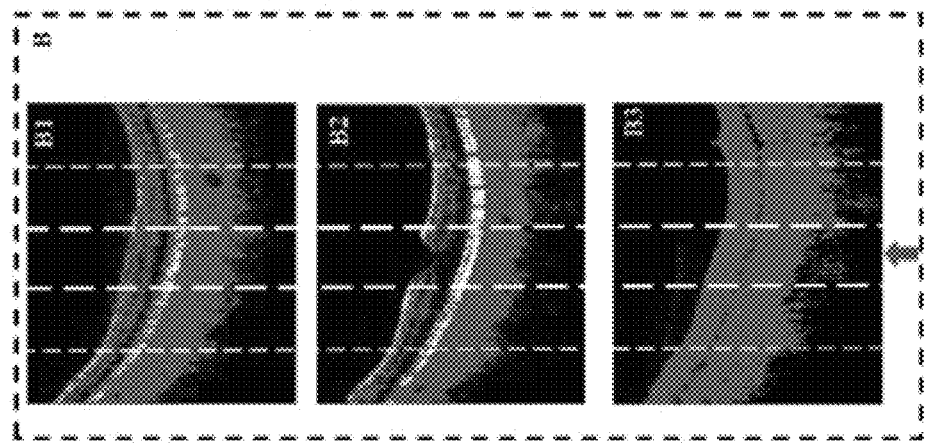
Figure 3B1　Figure 3B2　Figure 3B3
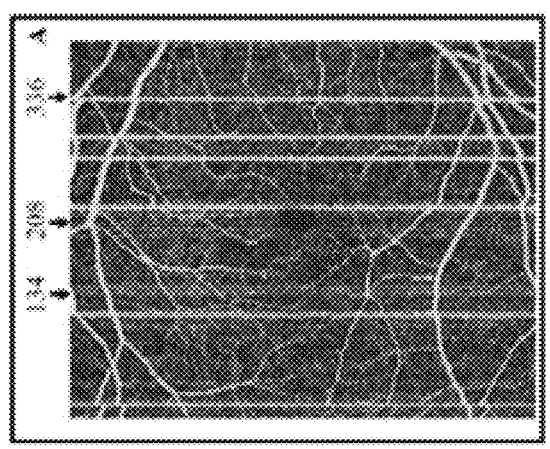
Figure 3A

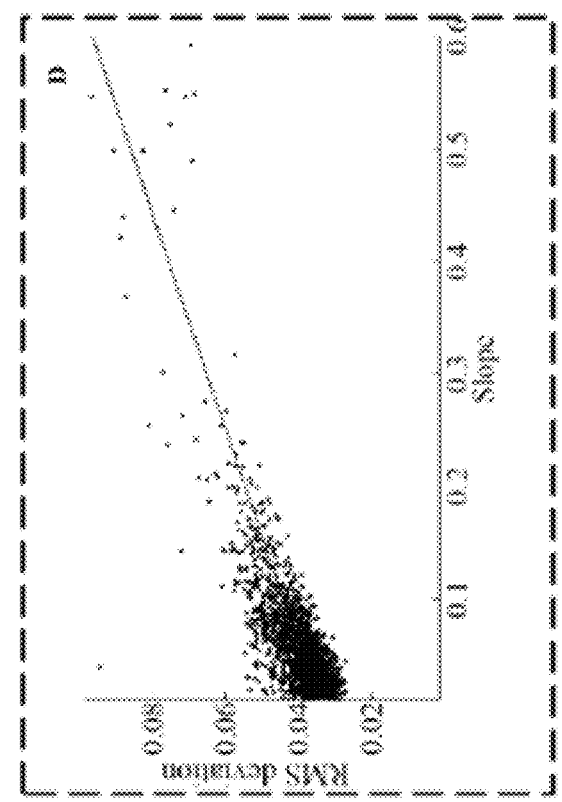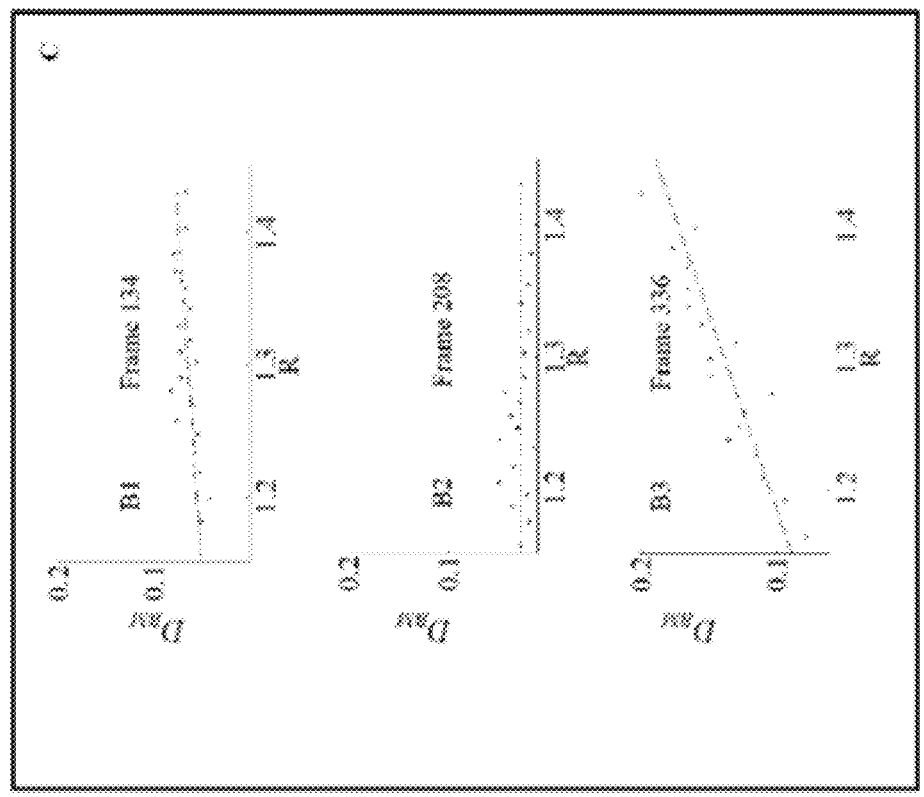
Figure 3C
Figure 3D

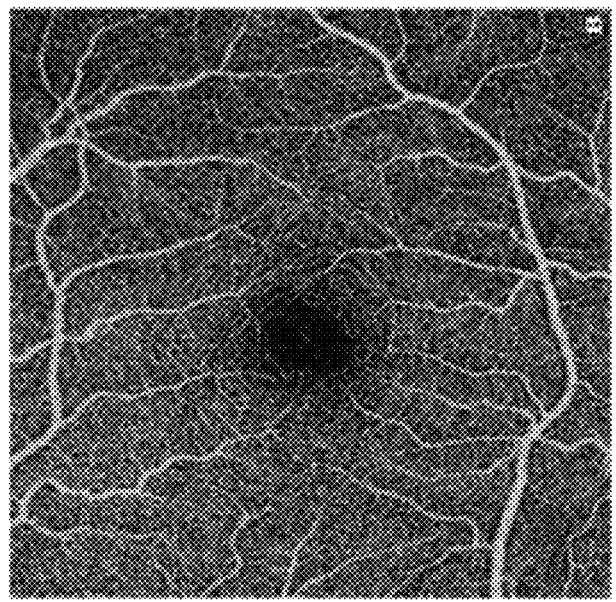
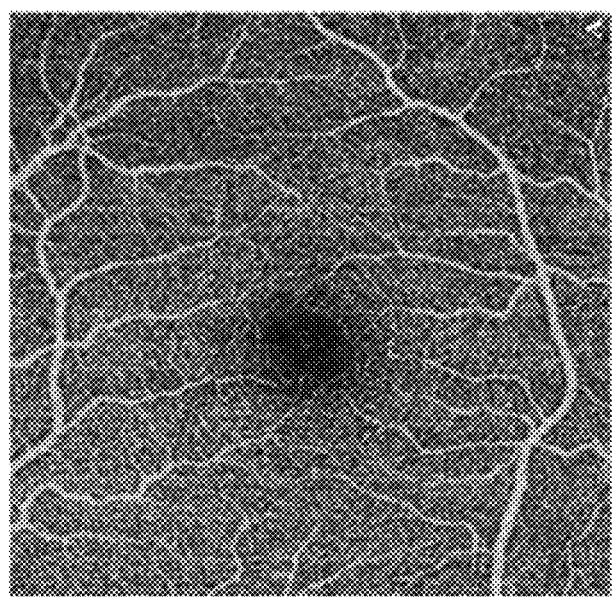
Figure 6A
Figure 6B

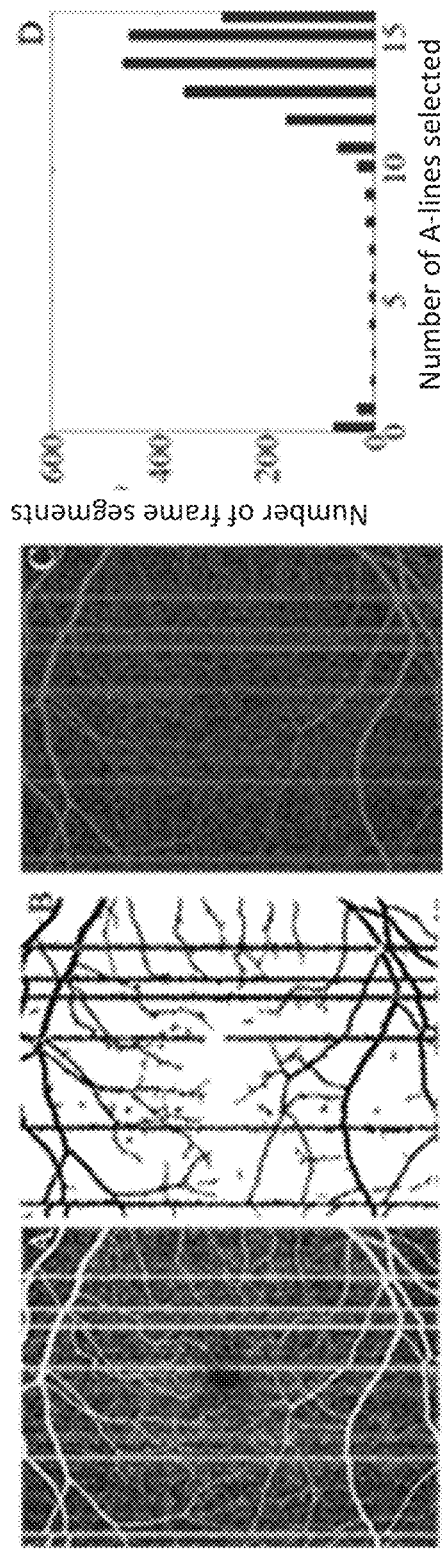

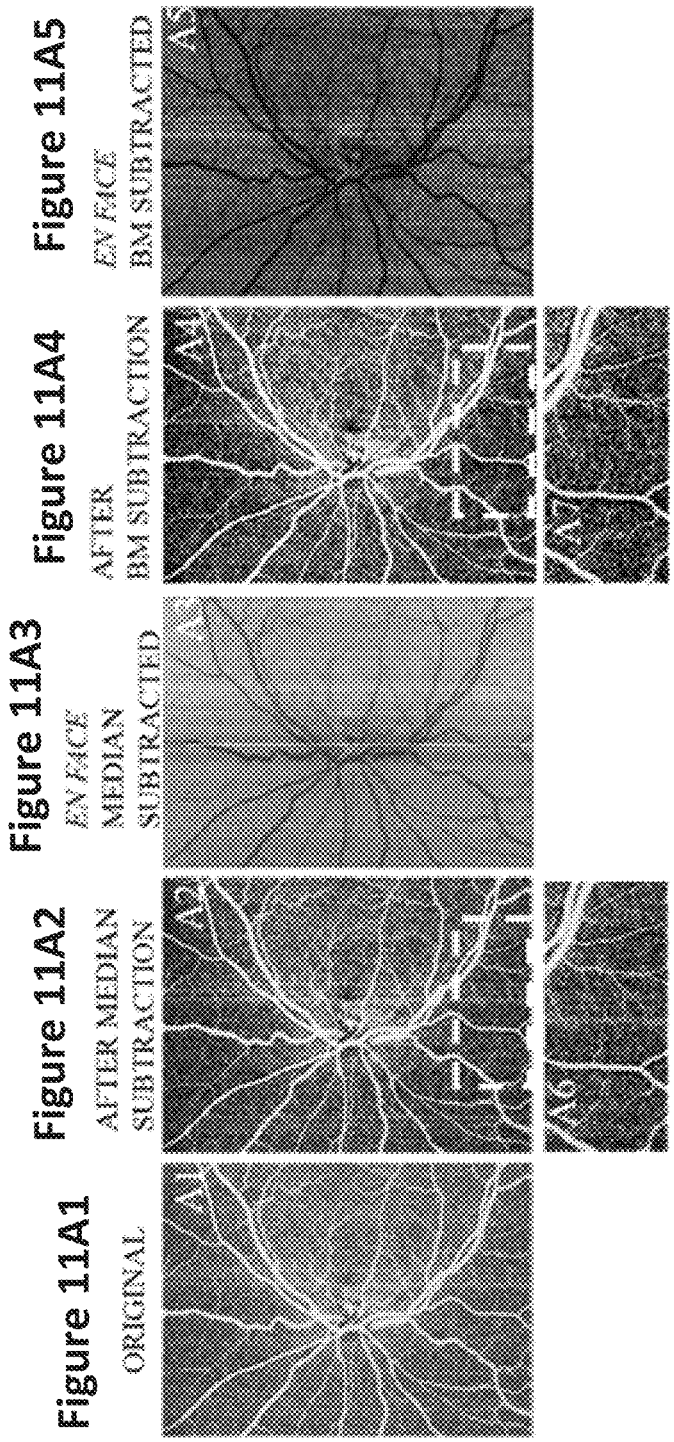
Figure 11A1 ORIGINAL
Figure 11A2 AFTER MEDIAN SUBTRACTION
Figure 11A3 EN FACE MEDIAN SUBTRACTED
Figure 11A4 AFTER BM SUBTRACTION
Figure 11A5 EN FACE BM SUBTRACTED
Figure 11A6
Figure 11A7

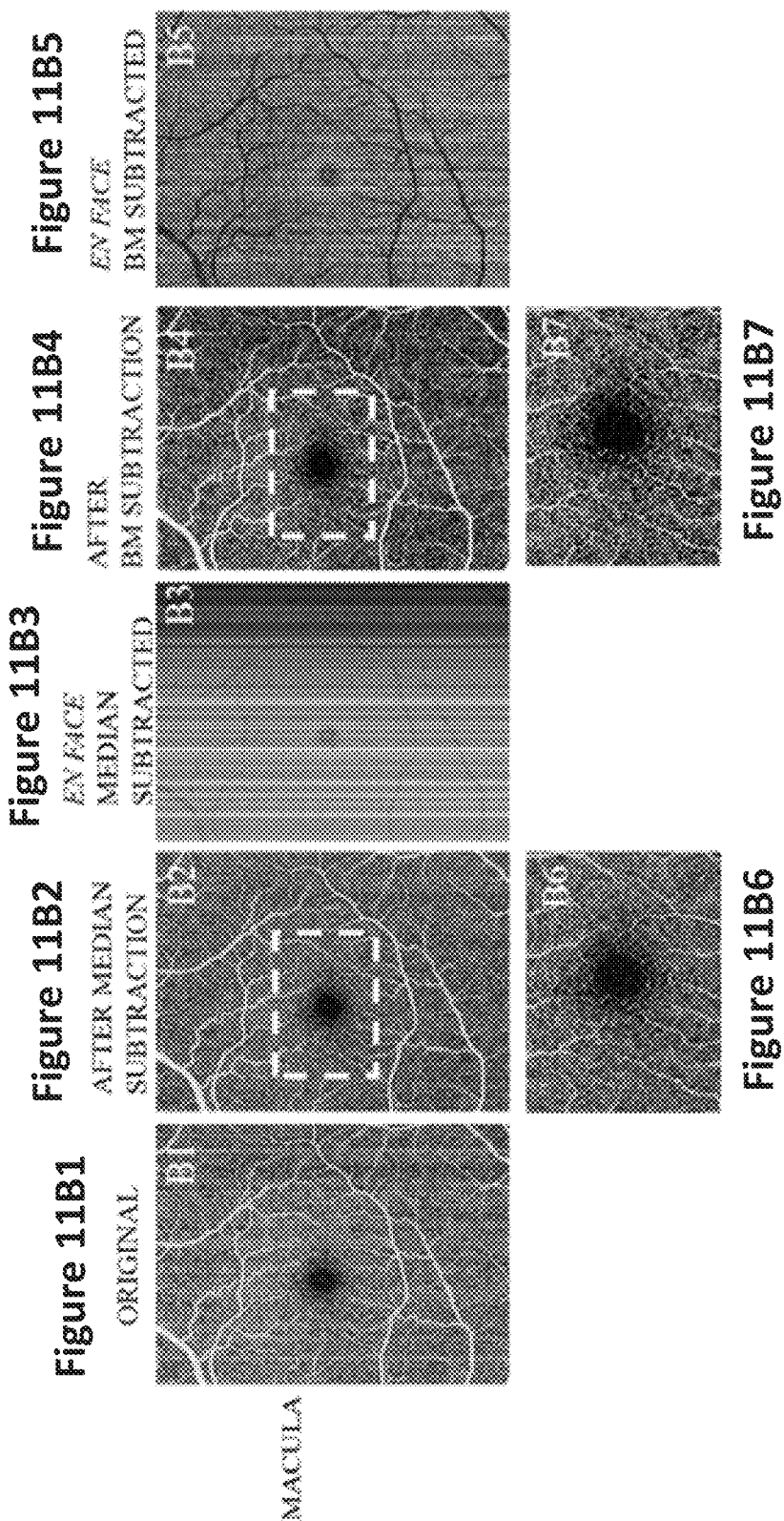

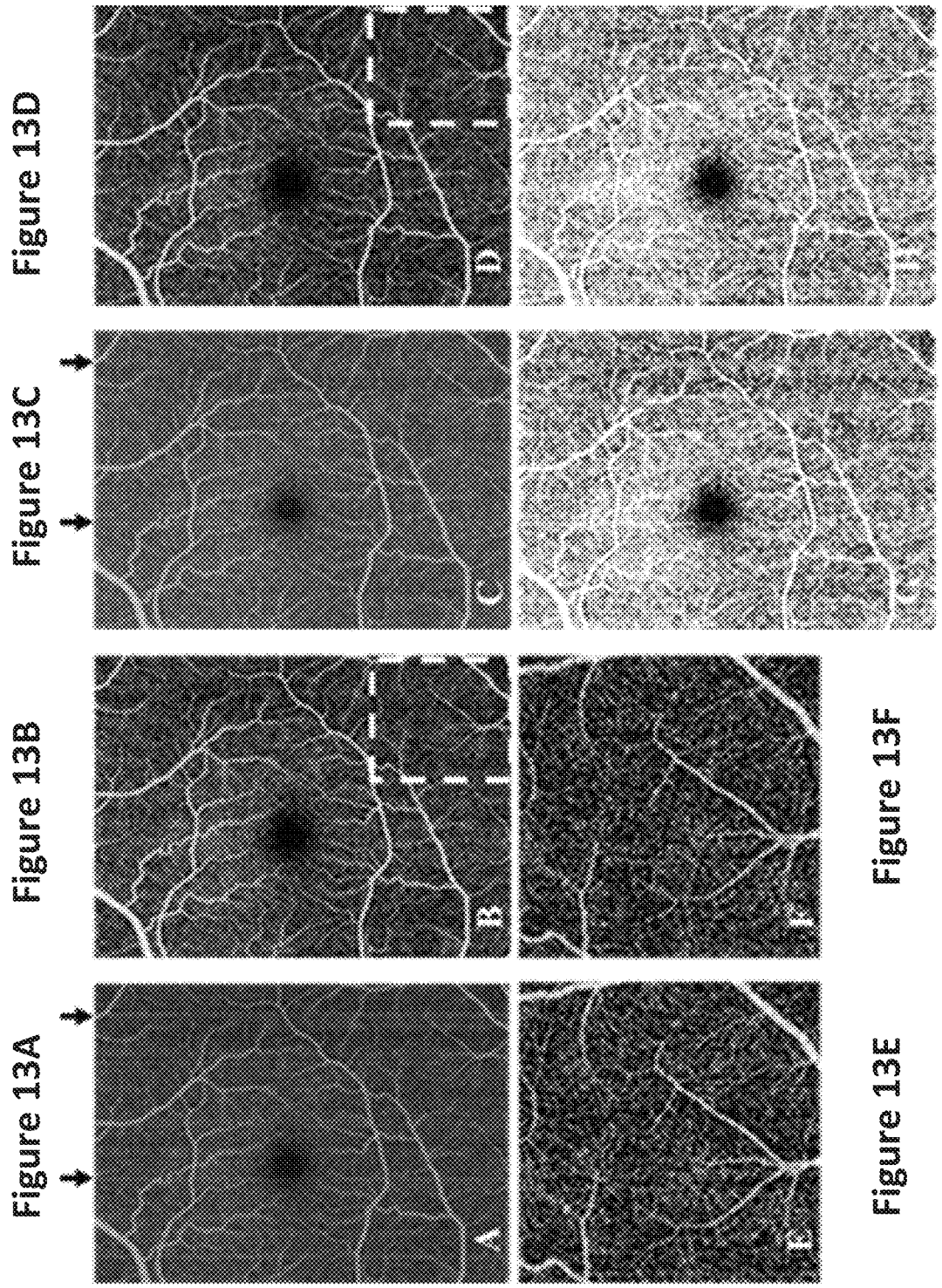

BULK MOTION SUBTRACTION IN OPTICAL COHERENCE TOMOGRAPHY ANGIOGRAPHY

CROSS REFERENCE TO RELATED APPLICATION

The present application claims priority to U.S. Provisional Patent Application No. 62/503,306, titled "REGRESSION-BASED TECHNIQUES FOR BULK MOTION SUBTRACTION IN OPTICAL COHERENCE TOMOGRAPHY ANGIOGRAPHY," filed May 8, 2017, the disclosure of which is hereby incorporated by reference in its entirety.

ACKNOWLEDGEMENT OF GOVERNMENT SUPPORT

This invention was made with government support under EY023285, EY018184, EY024544, and DK104397 awarded by the National Institutes of Health. The government has certain rights in the invention.

FIELD

Generally, the field involves optical coherence tomography (OCT) in angiography. More specifically, the field involves techniques for bulk motion subtraction in OCT angiography.

BACKGROUND

Optical coherence tomography (OCT) is an imaging modality for high-resolution, depth-resolved cross-sectional and 3-dimensional (3D) imaging of internal structures in biological tissue. OCT relies on the principle of low-coherence interferometry to measure light back-reflected from tissue structures at different depths. This means that the beam sampling the tissue interferes at the detector with a reference beam that travels the same distance and is back-reflected from a mirror. To obtain an OCT image, the instrument scans a light beam laterally, creating a series of axial scans (A-lines) that contains information on the strength of reflected signal as a function of depth. The combination of successive A-lines acquired at one lateral position (known as a B-scan) allows the visualization of a 2-dimensional section of the tissue anatomy, henceforth referred here as the cross-sectional image. Among its many applications, ocular imaging has found an extensive clinical use in the past years, both for the anterior (cornea and iris) and posterior (retina) sections.

Initially, imaging by OCT required a moving reference mirror to produce a depth-resolved reflectivity profile of the tissue under investigation. This modality is known as time-domain OCT. An alternative modality known as Fourier-domain OCT (FD-OCT) that uses a stationary reference mirror was later introduced. FD-OCT achieves depth-resolved imaging by separately measuring the interference of the spectral components of a broadband light source. This can be accomplished by either an incident broadband pulse of light that is later separated into its spectral components by a spectrometer or alternatively, by scanning the spectrum of a high-speed swept-source and measuring the interference signal with balanced photodetectors. With the advent of FD OCT, the allowed scanning speed increased tremendously and the potential for functional imaging (such as imaging vascular networks) could be realized.

Optical coherence tomography angiography (OCTA) is a noninvasive blood flow imaging technique based on OCT that allows depth-resolved visualization of vascular maps with capillary resolution. Flow detection using OCT was first demonstrated by Doppler OCT, a technique that images blood flow by evaluating phase differences between adjacent depth profiles. More recent OCTA algorithms on the other hand, rely on mathematical operations (e.g. decorrelation, variance, difference, or ratio) that quantify variations in the phase and/or amplitude of OCT signal between at least two consecutive B-scans acquired at the same raster position. For example, the speckle variance method computes the amplitude decorrelation between consecutive cross-sectional OCT images to identify variations in the intensity of the OCT signal due to the motion of blood cells. An improved version of the speckle variance method is the split-spectrum amplitude-decorrelation angiography (SSADA) algorithm, which splits the interferogram before computing the amplitude decorrelation and later averages the flow images generated by all spectral splits, enhancing the signal-to-noise ratio. SSADA uses only two B-scans at each lateral position, which is beneficial for a reduced scanning time. Another OCTA method referred to as split-spectrum amplitude and phase-gradient angiography (SSAPGA) exploits the phase of the OCT signal besides the amplitude to further improve the flow image quality. Yet another alternative that utilizes the complex OCT signal is known as optical microangiography and relies on a modified Hilbert transform to distinguish moving scatterers from static scatterers. All of these modalities have one common purpose, to exploit the larger variation in OCT signal between scans due to moving scatterers in order to represent the pixels corresponding to blood vessels brighter than the pixels representing the surrounding tissue.

Bulk motion of the eye generates variation in OCT signal that can be detected with the various OCTA algorithms. Currently, correction of bulk motion contribution to flow signal in OCTA is performed by an algorithm that subtracts the median decorrelation value of the retinal section of each B-frame.

BRIEF DESCRIPTION OF THE SEVERAL VIEWS OF THE DRAWINGS

FIGS. 3A, 3B1, 3B2, 3B3, 3C, and 3D demonstrate aspects of linear regression of decorrelation signal ($D_{BM}$) due to bulk motion as a function of the natural logarithmic tissue reflectance (R). FIG. 3A illustrates a 6 mm×8 mm (horizontal×vertical) OCTA scan (400 B-frames×850 pixels) from which frames 134, 208, and 336 are marked as examples for moderate, subtle, and high bulk motion, respectively. FIGS. 3B1, 3B2, and 3B3 show the cross-sectional B-scans of frames 134 (moderate bulk motion), 208 (subtle bulk motion) and 336 (high bulk motion near microsaccade), respectively. SSADA decorrelation signal is overlaid on top of the reflectance OCT signal. FIG. 3C shows the corresponding linear fit of the binned R vs. DBM for the central segment indicated by an arrow in FIGS. 3B1, 3B2, and 3B3. In FIG. 3D it is observed that the RMS deviation of un-binned D of non-flow voxels from the fitting curve found at each segment exhibit a linear dependence on the corresponding segment's slope, shown for all segments forming a volumetric scan.

FIG. 4A shows the original angiogram. FIG. 4B shows a skeletonized version of the original algorithm by applying the skeletonization algorithm separately on vessels of different calibers. FIG. 4C shows an inaccurate skeletonization obtained by applying the same algorithm directly on the original en face angiogram. Vessels of larger caliber on the upper left corner are almost indistinguishable.

In FIG. 5A, decorrelation due to bulk motion ($D_{BM}$) is modeled as a function of logarithmic reflectance R based on linear regression coefficients $m_k$ and $n_k$ from the regression analysis of the kth frame segment. Voxels with decorrelation value below threshold $D_{TH}$ (e.g., set at the 97.5 percentile of bulk motion (assuming normal distribution)) are classified as non-flow voxels. Accordingly, the corresponding decorrelation value D in the OCTA dataset is set to zero. The bulk motion-induced decorrelation in blood $D_{BM,blood}$ is calculated using the reflectance of blood obtained from the median reflectance of flow voxels (voxel with decorrelation value D above $D_{TH}$). Bulk motion velocity $v_{BM}$ is obtain from $D_{BM,blood}$ using Equation 2. In FIG. 5B, the bulk motion velocity is subtracted from a voxel with uncorrected decorrelation value $D_0$ and corresponding velocity $v_0$ that is high relative to the saturation velocity according to the nonlinear curve relating flow signal D to velocity. Therefore subtracting $v_{BM}$ from $v_0$ to obtained corrected velocity $v_1$ and corrected flow signal $D_1$ has little effect. In FIG. 5C, the bulk motion velocity is subtracted from a voxel with uncorrected decorrelation value $D_0$ and corresponding velocity $v_0$ that is lower than the saturation velocity. Here, subtracting $v_{BM}$ from $v_0$ to obtained corrected velocity $v_1$ and corrected flow signal $D_1$ has a larger effect than the previous example.

FIG. 6A illustrates an original (unprocessed) en face OCT angiogram of a macular scan generated by maximum projection of the inner retinal flow. FIG. 6B illustrates the en face OCT angiogram after processing by the bulk motion removal algorithm described herein.

FIGS. 8A-8D demonstration selection of the background A-lines, in accordance with various embodiments described herein. FIG. 8A demonstrates a 6×8 mm en face inner retinal angiogram on macula. FIG. 8B illustrates identification of A-lines containing large vessel flow signal or microsaccadic artifacts. FIG. 8C illustrates a map of the A-lines contained within the lowest 10 percentile of maximum projection values after removing the large vessel mask in FIG. 8B, overlaid on top of the en face angiogram. FIG. 8D illustrates the distribution of the number of A-lines selected for regression analysis in the 2000 segments.

FIG. 9A illustrates an en face image of an unprocessed macular scan. An arrow indicates the position of a frame of interest. Appearance of artefactual frames varied along the vertical axis due to changes in local reflectance. FIG. 9B illustrates the fitting slope of each of the five segments into which the frame is partitioned.

FIG. 10A illustrates an unprocessed en face retinal angiogram. FIG. 10B illustrates an en face retinal angiogram after removal of decorrelation signal from bulk motion voxels using a reflectance-adjusted threshold. FIG. 10C illustrates the difference between the angiograms of FIGS. 10A and 10B. FIG. 10D illustrates an en face retinal angiogram after subtraction of bulk motion velocity from the vascular voxels.

FIGS. 11A1-11A7 and 11B1-11B7 demonstrate a qualitative comparison between median subtraction and regression-based bulk motion subtraction in an optic disc scan (as shown in FIGS. 11A1-11A7) and a macular scan (as shown in FIGS. 11B1-11B7), in accordance with various embodiments. FIGS. 11A1 and 11B1 are unprocessed en face images. FIGS. 11A2 and 11B2 are scans after subtracting the median of the frame's retinal region. FIGS. 11A3 and 11B3 are obtained by subtracting FIGS. 11A1-11A2 and 11B1-11B2, respectively. FIGS. 11A4 and 11B4 are scans after regression-based bulk motion subtraction. FIGS. 11A5 and 11B5 are obtained by subtracting FIGS. 11A1-11A4 and 11B1-11B4, respectively. FIGS. 11A6 and 11A7 are close-ups of the 3.8 mm×1.7 mm sections enclosed by dashed lines on FIGS. 11A2 and 11A4, respectively. FIGS. 11B6 and 11B7 are close-ups of the 3.4 mm×2.5 mm sections enclosed by dashed lines on FIGS. 11B2 and 11B4, respectively.

FIG. 12A illustrates a reflectance image. FIG. 12B illustrates an unprocessed flow image. FIG. 12C illustrates a flow image after median subtraction. FIG. 12D illustrates a flow image after regression-based bulk motion subtraction, as described herein. FIGS. 12E and 12F are close-ups of the 1.3 mm B-scan sections enclosed by dashed lines in FIGS. 12C and 12D, respectively.

FIGS. 13A-13H demonstrate an investigation of the benefits of bulk motion pre-compensation by optimization of the bulk image shifts of the OCT images previous to OCTA processing, in accordance with various embodiments. FIG. 13A illustrates an en face original OCTA without pre-compensation. FIG. 13B illustrates an en face OCTA after regression-based bulk motion subtraction from the dataset used for FIG. 13A. FIG. 13C illustrates an original en face non-thresholded OCTA after inter-B-scan registration. FIG. 13D illustrates the result of applying the regression-based bulk motion subtraction on the dataset used for FIG. 13C. The residual artifacts still observed in FIG. 13B are better removed in FIG. 13D. FIGS. 13E and 13F are close-ups of the regions enclosed by dashed lines in FIG. 13B) and FIG. 13D, respectively. Better capillary-background contrast was observed in FIG. 13E. FIG. 13G is a binary vessel mask obtained by imposing a fixed threshold on FIG. 13C, while FIG. 13H is obtained by imposing a local regression-based threshold at each segment of a frame. Region enclosed shows that pre-compensation by inter-B-scan registration does not correct the vessel density dependence on local signal strength. Contrastingly, by a regression-based local thresholding a more homogeneous perfusion is identified for the whole scan.

DETAILED DESCRIPTION

Figure 1:
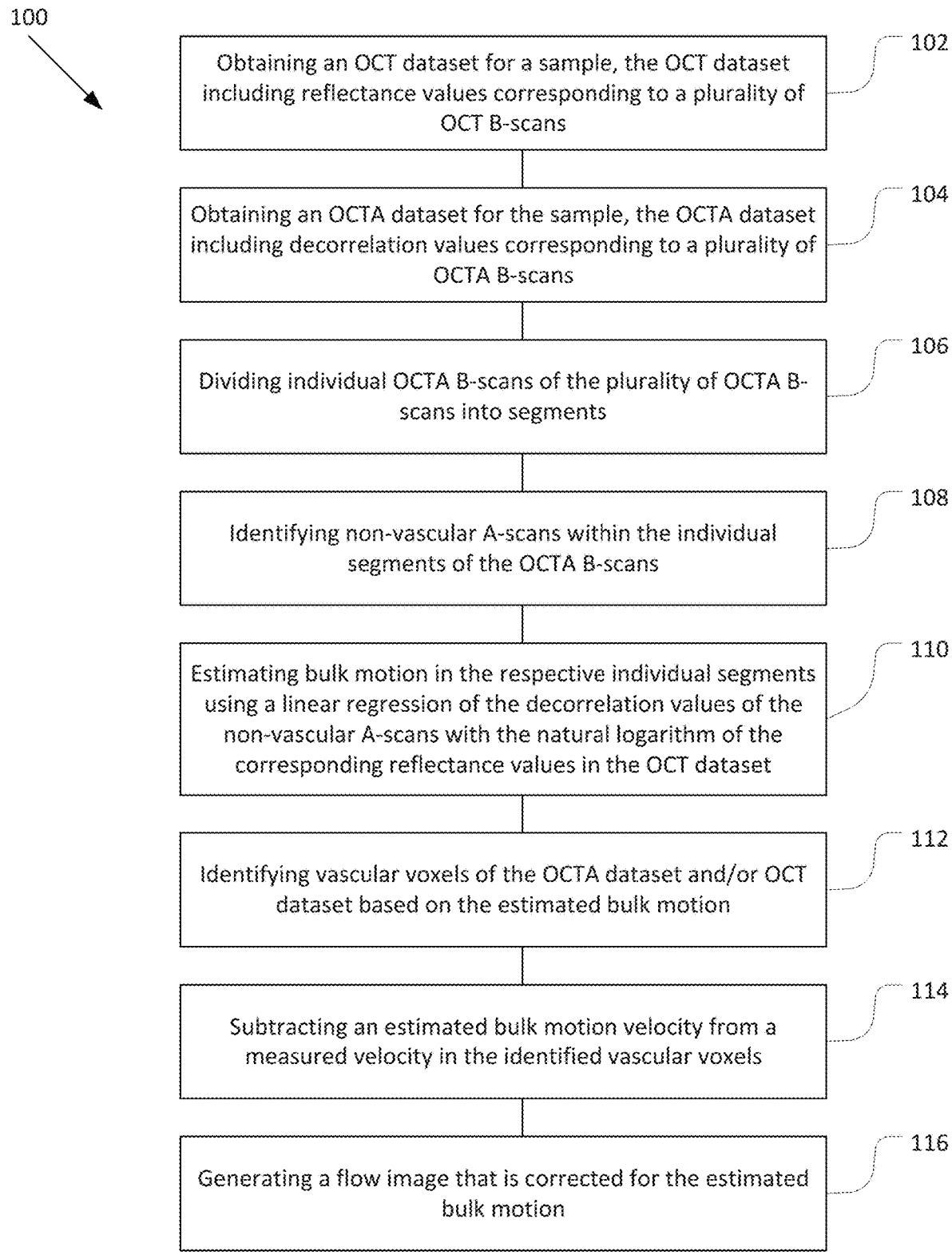
FIG. 1 is a flowchart that illustrates a method for bulk motion correction in optical coherence tomography angiography (OCTA), in accordance with various embodiments.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction). An A-scan may also be referred to as an A-line.

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image. A B-scan may also be referred to as a B-frame.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value or a decorrelation value). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined to form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset of decorrelation values reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a projection of the three dimensional dataset onto a single planar image called a 2D en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer can be used to generate a 2D en face angiogram of the inner retina). Once generated, the en face angiogram image may be used to quantify various features of the retinal vasculature as described herein. This quantification typically involves the setting of a threshold value to differentiate, for example, the pixels that represent active vasculature from static tissue within the angiogram. These 2D en face angiograms can be interpreted in a manner similar to traditional angiography techniques such as fluorescein angiography (FA) or indocyanine green (ICG) angiography, and are thus well-suited for clinical use. It is also common to generate 2D en face images from structural OCT data in a manner analogous to that used to generate 2D en face angiograms.

OCTA is typically sensitive to velocity ranges found in both large and small blood vessels down to the range of capillaries. The inter-scan time between consecutive B-frames determines the velocity range that the technique is sensitive to. This intrinsic motion contrast is a great advantage since it means that OCTA does not require injection of extrinsic contrast agents such as fluorescein dye into the blood stream. However, bulk motion of the eye also generates variation in OCT signal that can be detected with the various OCTA algorithms. Both fast bulk eye motions (e.g., saccades and microsaccadic) and slow eye motions (e.g., eye drift, eye tremor, and orbital pulsation) generate detectable OCTA signal. These can be considered as artifacts when the aim is to detect flow rather than bulk motion.

Some solutions exist to remove the effects of eye motion in OCTA images. Saccadic and microsaccadic motion generate very large OCTA signal as well as obvious disjunction between B-frames which are detected during image registration. In some techniques, these infrequent large motion artifacts are simply dealt with by removing the affected B-frames during the image registration processing. The missing B-frames are replaced by either an adjacent B-frame (e.g., if only one volume is being registered), or from another volume (e.g., if multiple volumetric scans are being registered and merged). In addition, tracking-assisted scanning schemes have been implemented to prevent scans from being recorded at all during blinks and microsaccades.

However, slow, small-amplitude bulk motion (BM) caused by ocular drift, pulsation, tremors or OCT system mechanical instabilities occur to some degree in nearly all B-frames and therefore cannot be dealt with by censoring B-frames (there would be little or no usable data left). Previously, this smaller background bulk motion signal had been estimated with the median value of the OCTA signal and subtracted from the entire OCTA B-frame. Although this simple median-subtraction algorithm does reduce bulk motion-induced OCTA signal (also referred to herein as noise to differentiate it from blood-flow generated OCTA signal), it is not entirely effective, as residual bulk motion can still be clearly seen on OCTA images as bright line artifacts. The reason is that bulk motion does not generate a constant OCTA signal (decorrelation value) that can be represented by the B-frame median. In fact, the present inventors have found that bulk motion noise varies across the B-frame (especially along B-frames with many axial scans), is approximately proportional to the logarithm of the reflectance signal, and is nonlinearly related to the combined velocity of flow and bulk motion.

Accordingly, described herein is an improved algorithm for removing bulk motion in OCT angiography. The bulk motion removal algorithm removes false flow signal (decorrelation) caused by bulk tissue motion during image acquisition, while preserving true flow signal in OCTA.

The bulk motion removal algorithm described herein more accurately removes bulk motion signal from the OCTA image, resulting in improved flow signal-to-noise ratio and image contrast. In addition, the bulk motion removal algorithm described herein provides accurate separation of vascular and nonvascular voxels which in turn improves the repeatability of vessel density calculation in healthy subjects. The continuity of vascular networks identified by the new algorithm is preserved, indicating accurate identification of vascular voxels.

The bulk motion removal algorithm may include dividing each OCTA B-frame into segments along the transverse dimension to obtain statistics on bulk motion-induced false flow signal (decorrelation). Previous algorithms used entire B-frames, which are too large to have uniform bulk motion. Diving B-frames into segments ensures that bulk motion is approximately uniform within the unit of analysis.

Additionally, or alternatively, the bulk motion removal algorithm described herein may use percentile analysis to select nonvascular A-lines for the estimation of bulk motion by regression analysis. This is an accurate way to automatically identify the nonvascular portion of the OCTA image.

Additionally, or alternatively, the bulk motion removal algorithm may use a regression model of bulk motion-associated false flow signal (decorrelation). Specifically, linear regression may be performed for decorrelation vs. the logarithmic reflectance signal in A-scans identified as nonvascular. Previous algorithms failed to account for the fact that bulk motion signal is proportional to reflectance on a logarithmic scale. Our algorithm use this relationship to model bulk motion more accurately.

Additionally, or alternatively, the bulk motion removal algorithm may separate nonvascular from vascular voxels using the regression model of bulk motion signal and estimated random noise that deviate from the model. This is an accurate automated method for separating vascular from nonvascular voxels. Unlike a previous method that used the foveal avascular zone to provide the separation threshold, the method described herein can work in scans of any anatomic region without relying on a specially identified avascular region.

Additionally, or alternatively, the bulk motion removal algorithm may subtract bulk motion velocity from vascular voxels using a nonlinear model that relates decorrelation signal to velocity. Laboratory studies showed that decorrelation is not linearly related to velocity (either due to flow or bulk motion), but reaches a plateau value above a saturation velocity. Therefore subtracting bulk motion velocity is more accurate than subtracting decorrelation values directly. This permits a more accurate calculation of flow index from regions of interest in the OCTA image.

Accordingly, the bulk motion removal algorithm may proceed with a series of operations to identify, quantify, and subtract bulk motion from OCTA signals. FIG. 1 illustrates a flow chart of a method 100 for bulk motion removal in OCTA, in accordance with various embodiments. At 102, the method 100 may include obtaining an OCT dataset for a sample (e.g., a retina), the OCT dataset including reflectance values corresponding to a plurality of OCT B-scans. At 104, the method 100 may include obtaining an OCTA dataset for the sample, the OCTA dataset including decorrelation values corresponding to a plurality of OCTA B-scans. For example, multiple OCT B-scans may be obtained at a same scan location, and the decorrelation values for a OCTA B-scan of the OCTA dataset may correspond to the decorrelation between reflectance values of the OCT B-scans associated with the same scan location.

At 106, the method 100 may include dividing individual OCTA B-scans of the plurality of OCTA B-scans into segments (e.g., along a transverse dimension). In some embodiments, the OCTA B-scans may first be divided into multiple tissue layers prior to segmentation.

At 108, the method 100 may include identifying nonvascular A-lines within the individual segments of the OCTA B-scans. At 110, the method 100 may include estimating bulk motion in the respective individual segments using a linear regression of the decorrelation values of the non-vascular A-lines with the natural logarithm of the corresponding reflectance values in the OCT dataset. In some embodiments, the bulk motion estimation may correspond to a bulk motion threshold. In some embodiments, the bulk motion threshold may be in a decorrelation domain. Additionally, or alternatively, the bulk motion threshold may be in a reflectance domain.

At 112, the method 100 may include identifying vascular voxels of the OCTA dataset and/or the OCT dataset based on the estimated bulk motion. For example, the vascular voxels may be identified as voxels of the OCTA dataset having decorrelation values greater than a bulk motion decorrelation threshold and/or voxels of the OCT dataset having reflectance values greater than a bulk motion reflectance threshold. The voxels that do not meet the threshold may be considered nonvascular, and as such only contain bulk motion. The nonvascular voxels may be set to a decorrelation value of zero in the OCTA dataset.

At 114, the method 100 may include subtracting estimated bulk motion velocity from the measured velocity in vascular voxels. The subtraction may be done in the velocity domain rather than the decorrelation domain.

At 116, the method 100 may include generating a flow image that is corrected for the estimated bulk motion. For example, as discussed above, the nonvascular voxels may be set to zero in the OCTA dataset. Additionally, the bulk motion velocity may be subtracted from the velocity of vascular voxels, and the corrected velocity may then be converted back to the decorrelation domain to generate a corrected decorrelation value. Alternatively, the flow image may be presented in the velocity domain.

Example implementations of various operations of the method 100 are discussed in more detail below. It will be apparent that some embodiments of the bulk motion removal method may modify or eliminate one or more operations, and/or add additional operations to the method 100. Additionally, in some embodiments, the operations may be performed in a different order, as appropriate.

Segmentation of the OCTA Dataset

Figure 2:
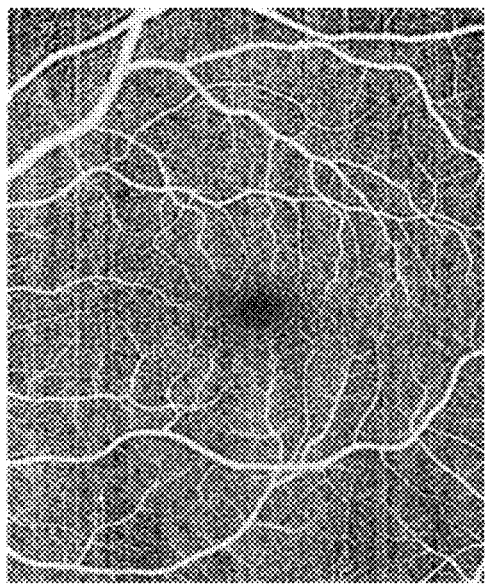
FIG. 2 is an en face angiogram of retinal flow by maximum projection of decorrelation values within a retinal slab, in accordance with various embodiments.

In some embodiments, prior to or as part of dividing the individual OCTA B-scans into segments (e.g., according to operation 106 of method 100), the anterior and posterior boundaries of the tissue (such as retina, cornea, or iris) as well as the boundaries between retinal layers may be identified on OCT reflectance B-frames. The general principle is to isolate the tissue layer (hereafter called slab) of interest for OCTA analysis. In the case of retinal tissue, the slab is defined between the vitreous/retina and the retina/choroid boundaries. The data from the OCT dataset and OCTA dataset corresponding to the slab may be isolated from the data corresponding to other regions. Identification and/or isolation of the slab may be performed by a directional-graph search method (e.g., as described in M. Zhang, J. Wang, A. D. Pechauer, T. S. Hwang, S. S. Gao, L. Liu, et al. "Advanced image processing for optical coherence tomographic angiography of macular diseases," Biomed Opt Express 6(12):4661-75 (2016), hereby incorporated by reference herein). Then an en face OCT angiogram is generated by assigning to each lateral position the maximum decorrelation value of the flow signal within the slab. An example of en face angiogram showing the retinal vascular network and containing bulk motion artifacts is shown in FIG. 2.

In various embodiments, the segmentation operation at 106 of the method 100 may include dividing the B-scans (also referred to as B-frames) of the OCTA dataset that correspond to the slab into a pre-defined number (e.g., 5) of equally sized segments. The segments may be small enough that the axial lines within them can be acquired within a small enough time frame (generally 1 millisecond or less) that bulk motion can be considered to be approximately constant within the segments.

Nonvascular Line Identification

At 108 of the method 100, the nonvascular A-lines within the individual segments of the OCTA B-scans are selected. In order to remove the signal due to bulk motion, the relationship of the reflectivity of the OCT signal to bulk motion should be determined in a region where bulk motion can be considered approximately constant. To recognize this relationship, voxels associated to nonvascular tissue only are selected and used to perform a linear regression analysis. Non-vascular voxels can be found anywhere in the slab, however, their flow signal contains artifactually large decorrelation values in the voxels located below vasculature, also known as projection artifact or decorrelation tail. Hence, for the sake of recognizing the decorrelation-reflectance relationship of bulk motion signal, it is beneficial to select data contained in A-lines completely devoid of vasculature within the slab of interest.

The retinal nonvascular A-lines (also referred to as background A-lines) are selected from each individual segment of the B-frame under analysis. The selection of a subset of non-vascular A-lines may be performed using multiple operations. First, the algorithm reads the en face angiogram. From this image, the A-scans containing information of large vessels are recognized and excluded, given that they certainly contain flow data. Large vessels can be automatically identified either from their large projected flow signal, their large vessel diameter by morphological operations or by applying a vesselness filter.

From the A-scans remaining after large vessel exclusion, a pre-determined percentage (e.g., 10%) of the A-scans having a lowest maximum decorrelation value among the A-scans of the segment may be identified as non-vascular A-scans. It is assumed that the frame segment is large enough so that the local vessel density does not exceed 90%. This percentage is approximately the upper boundary of inner retinal vessel densities among eight healthy subjects that participated in a study. This technique for identifying the non-vascular A-scans may be referred to as a percentile analysis.

In other embodiments, the non-vascular A-scans may be identified by identifying known non-vascular regions of the tissue such as the foveal avascular zone of the retina or by principal component analysis.

Bulk Motion Estimation Based on Regression Analysis

At 110 of the method 100, the bulk motion in the respective individual segments may be estimated using a linear regression of the decorrelation values of the nonvascular A-scans with the natural logarithm of the corresponding reflectance values in the OCT dataset. For implementation in anterior and posterior sections, the bulk motion removal algorithm recognizes the relation between decorrelation and reflectance of the voxels in previously identified non-vascular (background) A-lines. At each segment, the flow signal caused by bulk motion ($D_{BM}$) and the natural logarithm of the reflectance (R) of the selected background A-lines are read and concatenated into a single reflectance vector and a single decorrelation vector. The values in the reflectance vector are sorted by increasing reflectance and the decorrelation vector is sorted accordingly to preserve point-to-point correspondence. Both vectors are divided into a pre-defined number of bins (e.g., 5-50 bins, such as 20 bins). Values within each bin are averaged so that the resulting values in the binned reflectance vector are equidistant.

A linear regression routine is performed for all k frame segments to recognize the linear relationship between the binned reflectance and decorrelation vectors. The slopes ($m_k$) and intercepts ($n_k$) of the fits are saved. The slope of the fitting curve increases with the severity of the artifact (see FIGS. 3A, 3B1, 3B2, 3B3, and 3C). Since the linear relation recognized in this operation will be used in filtering out background noise as well as the subtraction of bulk motion from vascular voxels, this feature allows artifact selectivity in the subsequent thresholding and subtraction steps.

Also, the RMS deviation ($S_{BM}$) of the data from the fitting curve may be recorded for the un-binned data at each frame segment. The severity of the artifact may be associated to larger fitting slopes, and also to larger RMS deviations from the fitting curve. Hence, $S_{BM}$ values exhibited an approximately linear relationship to the slopes $m_k$ recognized in the regression routine (FIG. 3D). Due to occasional deviation outliers, it may be preferable to perform a second linear regression step, this time to recognize the global trend of the RMS deviation values versus $m_k$ values ($S_{BM\_k} = a + bm_k$) of all segments rather than using each segment's RMS deviation in the thresholding operation.

Thresholding Operation

In various embodiments, the background bulk motion decorrelation threshold $D_{TH}$ may be estimated according to Equation 1:

$$D_{TH}=(m_k R+n_k)+1.96(a+bm_k) \quad (1)$$

The first half of the threshold equation $(m_k R+n_k)$ is obtained from the regression of the binned decorrelation/reflectance of the $k^{th}$ segment as described above. The value R corresponds to the voxels' reflectance value. While $m_k$ and $n_k$ are the same for the whole segment, R is different for each voxel in the segment. The second half of the threshold equation $(1.96(a+bm_k)$ is the RMS deviation value calculated by the second regression operation described above, considering the $m_k$ value associated to the $k^{th}$ segment. Here, a and b are the same for the whole volume and the second part of the threshold equation is the same for all voxels in a frame segment. This threshold is applied to the OCTA data set (the volumetric flow data set) and all voxels with decorrelation values lower than their corresponding $D_{TH}$ are set to zero.

Conventionally, the vascular pixels in en face images are recognized from the background by setting a threshold dependent on the signal found in the foveal avascular zone (FAZ). This thresholding scheme can be used to quantify the vessel density, a parameter of clinical relevance. Such approach has two main disadvantages with respect to the thresholding scheme proposed in this invention. First, for scans in regions that do not contain the FAZ, such threshold would need to be obtained from a different scan where the FAZ is present. Second, quantification accuracy is dependent on signal strength. In the thresholding scheme described herein, there is no need to take a background reference from the foveal avascular zone, allowing identification of vascular from nonvascular voxels in scans of any region.

Figures 4A, 4B, 4C:
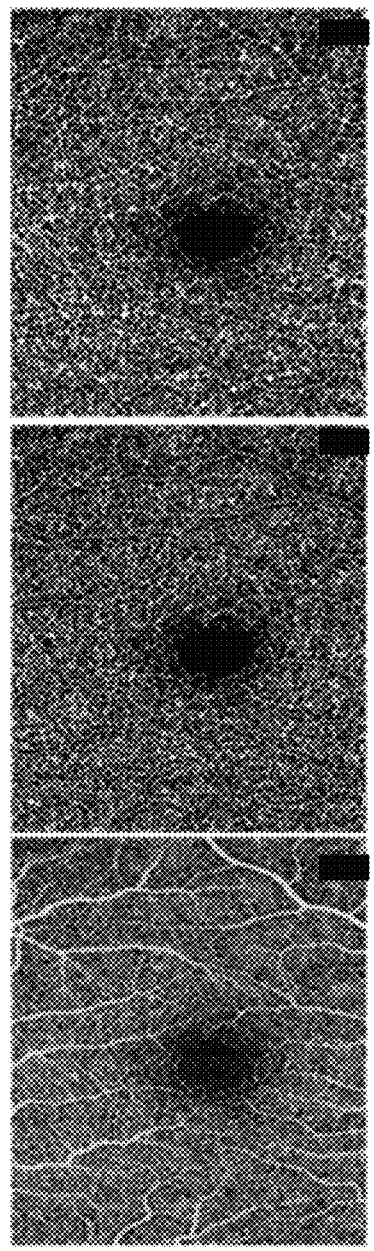
FIGS. 4A-4C demonstrate skeletonization of an en face angiogram using close up views of the foveal region for better visualization.

The thresholding operation described herein preserved the vascular integrity on en face angiograms. This was assessed using the vascular connectivity parameter, defined in a skeletonized version of the en face angiogram by the percentage of flow pixels contained in groups larger than five. Skeletonization of en face OCTA is the process of converting vessels into lines with a one-pixel width. Since en face retinal angiograms contain vasculature of different dimensions (see FIG. 4A), skeletonization may be performed separately for large vessels and capillaries. If vessels with different calibers were not skeletonized separately, inaccuracies in the recognition of large vessels sometimes would be manifested (see FIGS. 4B-4C). FIG. 4B shows a skeletonized version of the original algorithm by applying the skeletonization algorithm separately on vessels of different calibers. FIG. 4C shows an inaccurate skeletonization obtained by applying the same algorithm directly on the original en face angiogram. Vessels of larger caliber on the upper left corner are almost indistinguishable. An example skeletonization algorithm that may be used is described in R. M. Haralick and L. G. Shapiro, Computer and Robot Vision (Addison-Wesley Longman Publishing Co., Inc., 1992), p. 630, hereby incorporated by reference.

In a study performed by the present inventors, no significant deterioration of vascular connectivity was observed in scans performed on eight healthy volunteers (p>0.1).

Flow Velocity Correction

After the thresholding operation only vascular voxels should remain in the volumetric flow dataset. However, their decorrelation values contain information of bulk motion besides that of blood cells motion. Therefore, the frames affected by larger bulk motion at this point still appear brighter than the neighboring frames and the bulk motion needs to be subtracted from decorrelation values. However, the effect of bulk motion is not the same for all flow voxels in a frame segment. Instead, the bulk motion contribution to decorrelation signal at capillaries is significantly higher than the contribution of the same motion at large vessels, where decorrelation saturates (see FIGS. 5B-5C).

Because decorrelation is not linearly related to velocity, the subtraction of the bulk motion contribution must be performed in the velocity domain rather than in the decorrelation domain. For this purpose, described herein is a method to estimate the bulk motion velocity from frame segments. The velocity value is the same for all voxels in a segment and can be estimated using a nonlinear model that relates decorrelation and velocity as shown in Equation 2:

$$v_{BM} = -\frac{1}{3} v_{sat} \ln\left(1 - \frac{D_{BM,blood} - D_{brownian}}{D_{sat} - D_{brownian}}\right) \quad (2)$$

In one example of this model, the saturation value $D_{sat}$ is defined as 0.95 times the 99th percentile of the flow signal in the en face angiogram. $D_{brownian}$ is estimated assuming that it maintains the same proportion to $D_{sat}$ as the one reported previously. The value of the saturation velocity $v_{sat}$ may be approximated utilizing experimental data (e.g., as obtained in J. P. Su, R. Chandwani, S. S. Gao, A. D. Pechauer, M. Zhang, J. Wang, Y. Jia, D. Huang, and G. Liu, "Calibration of optical coherence tomography angiography with a microfluidic chip," J Biomed Opt 21, 086015-086015 (2016), hereby incorporated by reference herein). The experimental data may be adjusted for the difference in inter-scan period between the OCT system used to obtain the experimental data and the OCT system being used at present. The variable $D_{BM,blood}$ is calculated from the D vs. R linear regression recognized for each segment, using the median reflectance of the flow voxels ($R_{blood}$ in FIG. 5A).

In various embodiments, the velocity $v_0$ estimated for each vascular voxel is found using each voxel's decorrelation value $D_0$ instead of $D_{BM,blood}$ in Equation 2. The bulk motion velocity $v_{BM}$ of the segment is then subtracted from the velocity calculated at each voxel. Then, by inverting the nonlinear model (see Equation 3 below), the decorrelation values free of bulk motion contributions are obtained. Accordingly, this mechanism prevents excessive subtraction from voxels representing high-speed flow, where the impact of bulk motion on decorrelation value is significantly lower.

$$D_1 = (D_{sat} - D_{brownian})\exp\left(-3\frac{v_0 - v_{BM}}{v_{sat}}\right) + D_{brownian} \quad (3)$$

Generation of Flow Image

FIG. 6A illustrates an original (unprocessed) en face OCT angiogram of a macular scan. FIG. 6B illustrates the en face angiogram after processing by the bulk motion subtraction algorithm described herein. Besides foveal cleanup, artifact appearance has been corrected and the contrast between capillaries and background has been improved.

EXAMPLES

The following examples are illustrative of the disclosed method. In light of this disclosure, those skilled in the art will recognize that variations of these examples and other examples of the disclosed method would be possible without undue experimentation.

Example 1

Study to Test Regression-Based Algorithm for Bulk Motion Subtraction in Optical Coherence Tomography Angiography Methods Data Acquisition Volumetric OCTA scans of the macula and the optic disc of healthy subjects were acquired using a wide-field 200-kHz OCT system. The system relies on a swept-source configuration that utilizes a tunable laser (Axsun, Inc., Billerica, Mass., USA) operating at 1044 nm center wavelength with a 104 nm tuning range. It has a lateral resolution of 12 µm and an axial resolution of 7.5 µm, which is increased to 22.5 µm on the flow image. Participants were recruited at the Casey Eye Institute of OHSU and informed consent was obtained. The protocol was approved by the Institutional Review Board/Ethics Committee of OHSU and adhered to the tenants of the Declaration of Helsinki in the treatment of human participants. The scan pattern consisted of 800 B-frames composed of 850 A-lines and located at 400 raster positions (y-priority), covering an 8×6 mm² area. Each B-scan was completed in 4.75 ms.

Data Processing

Data was processed using the Matlab 2013a release (Mathworks, Natick, Mass., USA). Cross-sectional OCT images were generated and B-frames acquired at the same raster position were averaged. OCTA data was calculated using the SSADA algorithm. Segmentation of the vitreous and inner limiting membrane (ILM) interface, outer plexiform layer (OPL) and outer nuclear layer (ONL) interface as well as Bruch's membrane and choroid interface was automatically performed by a directional graph-search algorithm. The region contained between ILM and OPL is the vascularized inner retina. En face images were generated by maximum projection of the flow signal within the inner retinal slab. An expert grader manually corrected segmentation errors.

Frames affected by microsaccadic artifacts were recognized on the en face OCTA image by identifying summed flow signal above a threshold, and excluded from analysis. The relationship between bulk motion contribution to decorrelation signal and the local reflectance was recognized. Because decorrelation is not linearly related to velocity, the subtraction of the bulk motion contribution must be performed on the velocity domain rather than in the decorrelation domain. Non-microsaccadic frames were divided into 5 segments where local reflectance does not vary abruptly. The segments are small enough that the axial-lines within them could be acquired within a small enough time frame (less than 1 millisecond) that bulk motion could be considered to be approximately constant within the segments. Then, a method to estimate the bulk motion velocity from frame segments was performed, as described herein.

At each segment, a group of A-lines devoid of inner retinal flow voxels was selected. For this purpose, A-lines crossing large vessels were first identified by a binary large vessel mask of the en face angiogram and excluded from the following analysis. The mask was constructed by successively applying amplitude thresholding to remove the majority of capillary pixels, a morphological opening (erosion followed by dilation) to cleanup dispersed pixels, a Gaussian convolution filter to prevent holes in the middle of large vessels and a final binarization step. From the remaining A-lines, the first 10 percentile with the lowest decorrelation signal were selected, assuming these are composed by non-flow voxels only. The threshold chosen is approximately the upper boundary of inner retinal vessel densities among the healthy subjects that participated in the study. The decorrelation and natural logarithm of the reflectance data selected in the segment were converted into vectors and sorted by increasing order of reflectance values. Then, the vectors were divided into 20 equally sized bins and the reflectance and decorrelation values in each bin were averaged, forming the new vectors $D_{bin}$, $R_{bin}$. The slope ($m_k$) and intercept ($n_k$) of the $D_{bin}=f(R_{bin})$ linear relationship were identified and recorded for all k=2000 segments. The slope of the linear fit was larger at frames with larger prevalence of motion, as shown in FIGS. 3A-3C. The RMS deviation ($S_{BM}$) of the un-binned data was also recorded at each segment. Another linear regression fitting was performed to recognize the relationship between the deviation $S_{BM}$ and the slopes $m_k$ of all segments forming a volumetric scan, expressed as $S_{BM}=a+bm_k$ (see FIG. 3D). Then, the voxels in the $k^{th}$ segment with decorrelation below the threshold defined in Equation 1 (which is repeated below) were set to zero. In frames affected by microsaccadic artifacts no A-lines were selected, the regression analysis step was skipped and the decorrelation values of all voxels were also set to zero. Fitting parameters in segments with less than five A-lines selected for regression analysis were substituted by the parameters of the neighboring segment within the same B-frame.

$$D_{TH}=(m_k R+n_k)+1.96(a+bm_k) \quad (1)$$

Figure 5A:
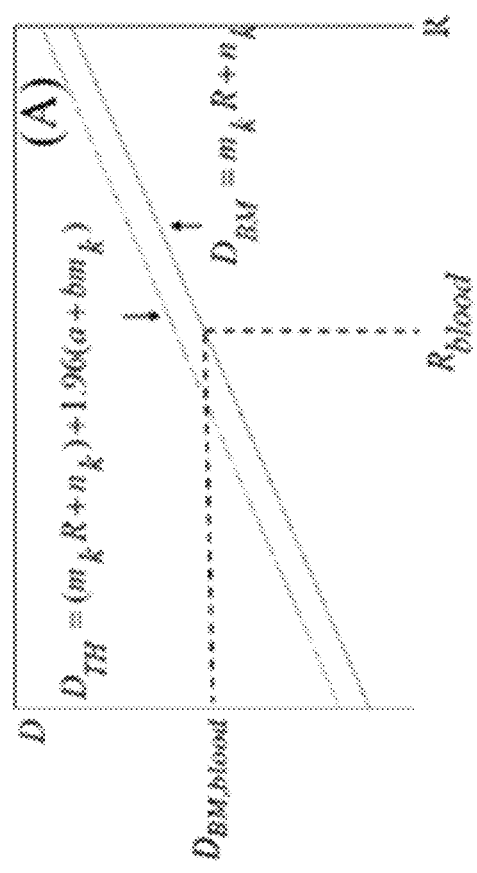
FIGS. 5A-5C demonstrate removal of bulk motion contribution to vascular voxels within each B-frame segment.
Figure 5C:
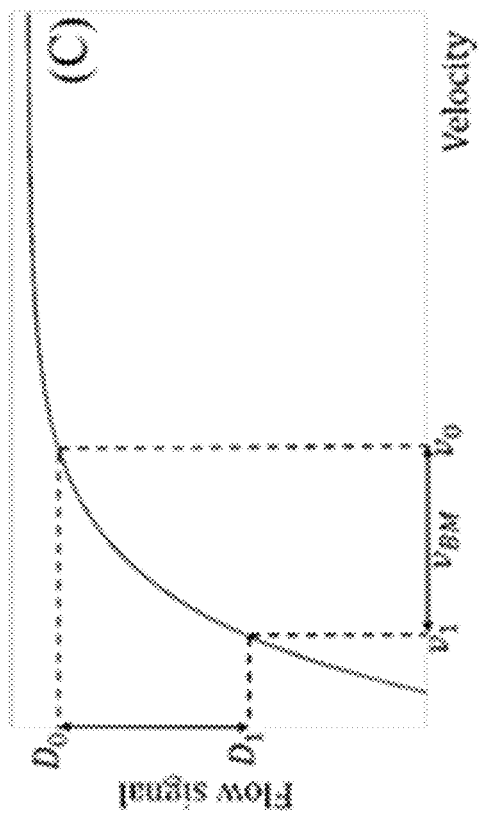
Figure 5B:
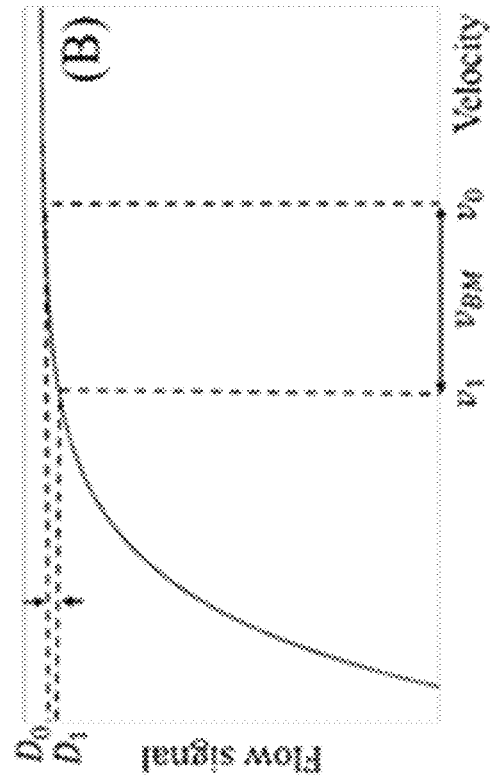

Vascular voxels remain after thresholding, and the contribution of bulk motion $D_{BM,blood}$ to their flow signal was obtained using the median reflectance of the flow voxels within the frame segment ($R_{blood}$ in FIG. 5A). An estimate of bulk motion velocity was calculated by a nonlinear model that related decorrelation and velocity in laboratory blood flow phantoms (as shown in Equation 2, repeated below).

$$v_{BM}=-\frac{1}{3}v_{sat}\ln\left(1-\frac{D_{BM,blood}-D_{brownian}}{D_{sat}-D_{brownian}}\right) \quad (2)$$

The saturation value $D_{sat}$ was calculated as 0.95 times the $99^{th}$ percentile of the flow signal in the en face angiogram. $D_{brownian}$ was estimated assuming that it maintains the same proportion to $D_{sat}$ as the one reported in J. P. Su, R. Chandwani, S. S. Gao, A. D. Pechauer, M. Zhang, J. Wang, Y. Jia, D. Huang, and G. Liu, "Calibration of optical coherence tomography angiography with a microfluidic chip," J Biomed Opt 21, 086015-086015 (2016), incorporated by reference herein. The value of the saturation velocity $v_{sat}$ was approximated utilizing the experimental data obtained in the previously cited reference, adjusting for the difference in inter-scan period between the Avanti RTVue-XR (Optovue, Inc. Fremont, Calif., USA) and the wide-field system used in this Example. Equation 2 was also used to calculate a velocity $v_0$ for each original decorrelation value $D_0$. Voxels with decorrelation above $D_{sat}$ cannot be converted to velocity domain by Equation 2 and were assigned $D_{sat}$ and $v_{sat}$ values. The calculated $v_{BM}$ was subtracted from $v_0$ at every vascular voxel and the bulk motion-free decorrelation $D_1$ was obtained by Equation 3 (repeated below). This mechanism prevented excessive subtraction from voxels representing high-speed flow, where the impact of bulk motion on decorrelation value is significantly lower (see FIGS. 5B-5C).

$$D_1 = (D_{sat} - D_{brownian})\exp\left(-3\frac{v_0 - v_{RM}}{v_{sat}}\right) + D_{brownian} \quad (3)$$

Figure 7:
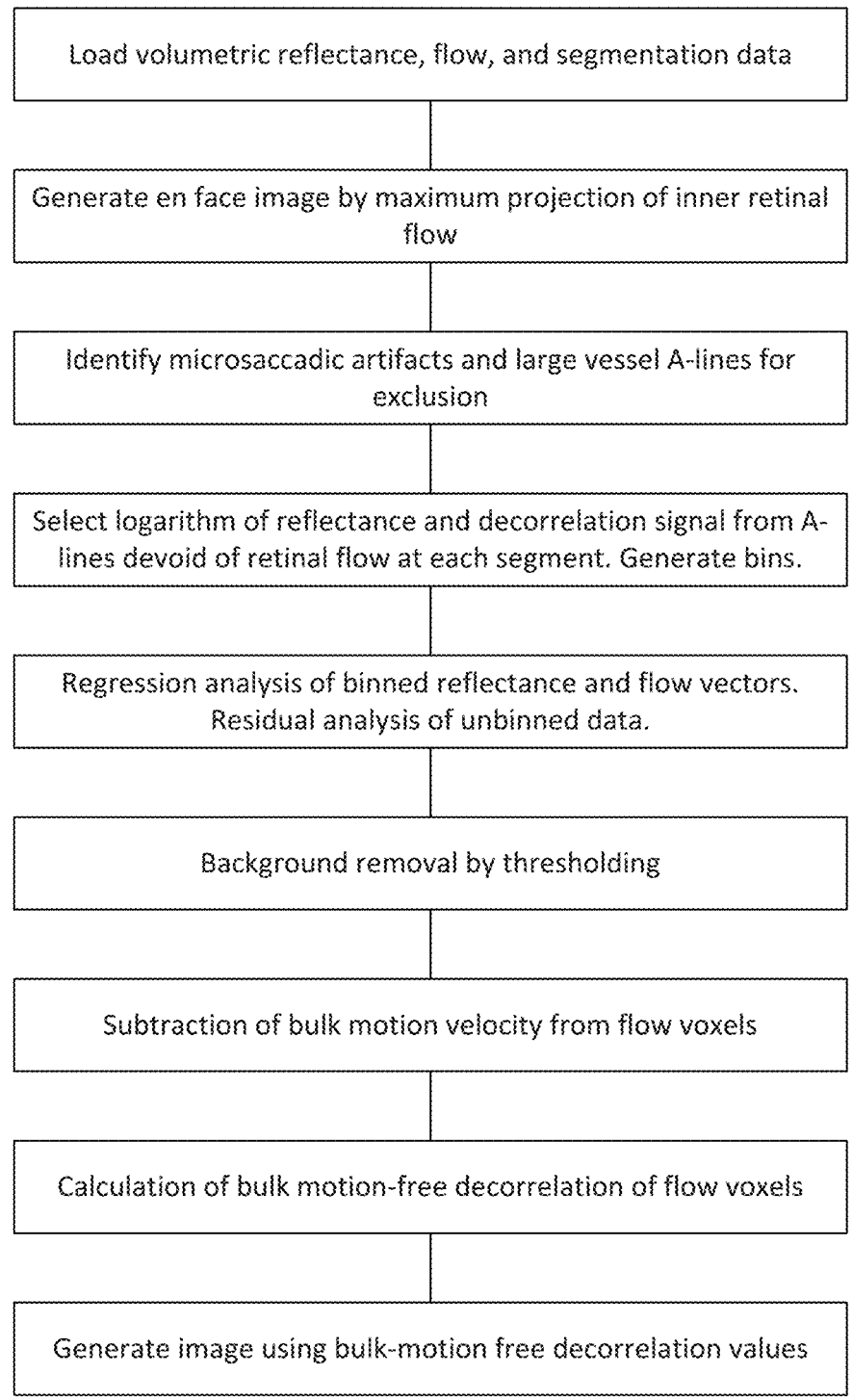
FIG. 7 is a flow chart of the bulk motion removal method used in an example study in accordance with various embodiments described herein.

A flow diagram of the bulk motion removal method used in the study of Example 1 is shown in FIG. 7.

Comparison to Median Subtraction Algorithm

The regression-based bulk motion subtraction method described herein was compared with an earlier method in which the median decorrelation value of the segmented retinal region was subtracted from all retinal voxels within the B-frame segments defined above. The threshold used to distinguish vascular from non-flow pixels in original and median-subtracted angiograms was obtained from the decorrelation at the foveal avascular zone (FAZ) of en face projections by $D_{flow} = \overline{D}_{FAZ} + 2.33\sigma_{D_{FAZ}}$, where $\overline{D}$ and $\sigma$ represent mean value and standard deviation.

Comparison to Inter-B-Scan Registration Algorithm

An alternative approach to bulk motion removal is to compensate the bulk motion between consecutive B-scans prior to computing OCTA flow signal. The benefits and tradeoffs of this pre-processing step in improving the artifact removal efficacy by the regression-based bulk-motion subtraction algorithm were evaluated.

For inter-B-scan registration we applied in SSADA a method similar to the one proposed in J. Lee, V. Srinivasan, H. Radhakrishnan, and D. A. Boas, "Motion correction for phase-resolved dynamic optical coherence tomography imaging of rodent cerebral cortex," Opt Express 19, 21258-21270 (2011), incorporated by reference herein. Briefly, OCT images were first up-sampled by a factor of two in lateral (x) and axial (z) dimensions. An iterative routine maximizes the cross-correlation of the OCT signal of the two B-scans acquired at each position by rigid displacements of the second B-scan in two directions. After recognizing the optimal shift, it was applied to the second OCT image of each of the 11 pairs generated by spectrum splitting (as described in S. S. Gao, G. Liu, D. Huang, and Y. Jia, "Optimization of the split-spectrum amplitude-decorrelation angiography algorithm on a spectral optical coherence tomography system," Opt Lett 40, 2305-2308 (2015)). Finally, the OCT images were down-sampled and the amplitude decorrelation signal was computed.

Image Quality Assessment

Bulk motion subtraction efficiency was assessed by the percentage of average FAZ signal remaining within the segmented retinal slab after processing the original data.

Parafoveal signal-to-noise ratio (SNR) was calculated by Equation (4). The parafoveal annulus is concentric with the fovea, has an outer diameter of 2.5 mm and an inner diameter of 0.6 mm.

$$SNR = \frac{\overline{D}_{parafoveal} - \overline{D}_{FAZ}}{\sigma_{D_{FAZ}}} \quad (4)$$

Vessel density was defined for en face projection as the percentage of area occupied by vascular pixels within the parafovea. Its coefficient of variation was used to assess inter-scan vessel density repeatability.

The RMS image contrast was defined as the standard deviation of the en face flow image, expressed in Equation 5:

$$C_{RMS} = \sqrt{\frac{1}{A} \times \sum_{(x,y) \in A} (D(x,y) - \overline{D})^2} \quad (5)$$

Preservation of the vascular integrity after bulk motion subtraction was assessed by the vascular connectivity, defined in a skeletonized version of the en face angiogram by the percentage of flow pixels contained in groups larger than five. Skeletonization of en face OCTA is the process of converting vessels into lines with a one-pixel width. It was performed by the function bwmorph included in Matlab's Image Processing Toolbox. This function relies on an algorithm that iteratively removes pixels on boundaries of objects recognized on a binary image until the objects remain unchanged. Since en face retinal angiograms contain vasculature of different dimensions (FIG. 4A), skeletonization was performed separately for large vessels and capillaries. If vessels with different calibers were not skeletonized separately, inaccuracies in the recognition of large vessels sometimes would be manifest (see FIGS. 4B-4C).

The p-value of a paired sample t-test evaluated the statistical significance of the results.

Results

Optic disc and macula from eight healthy volunteers were imaged. Scans containing microsaccadic artifacts crossing the parafoveal annulus were processed by the algorithm but excluded from the quantitative analysis.

A-lines containing microsaccadic artifacts and large vessels were successfully recognized (FIG. 8A). The background A-lines selected at each segment avoided those containing vascular information (FIG. 8C). Segments where the fitting parameters had to be obtained from adjacent segments due to the small number of background A-lines available never represented more than 3% of the total. Segments with no A-lines selected were located at the microsaccadic artifacts.

Figures 9A, 9B:
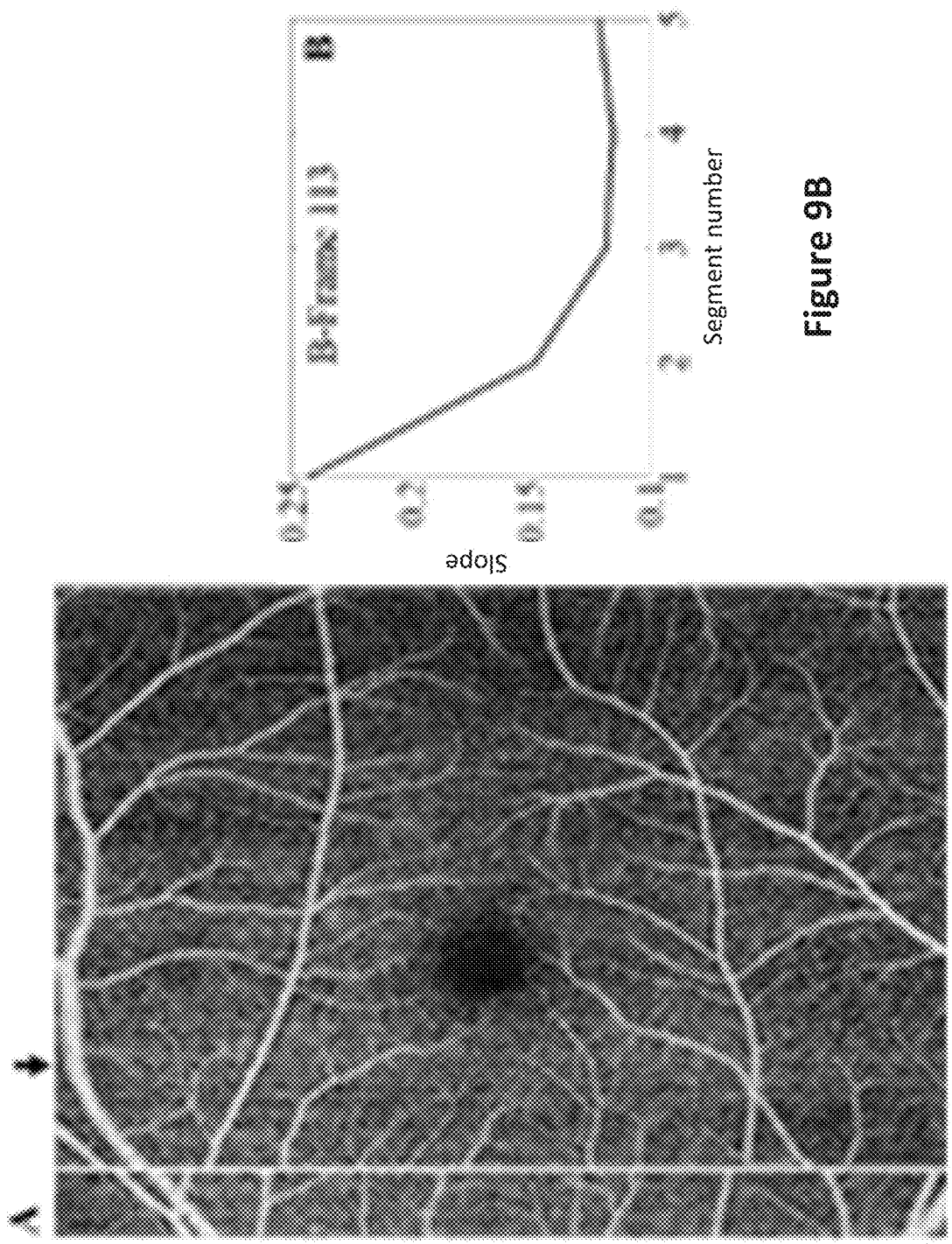
FIGS. 9A and 9B demonstrate within-frame variation of bulk motion, in accordance with various embodiments described herein.

Changes in bulk motion background signal could be observed by simple inspection of wide-field frames affected by moderate bulk motion on en face images (FIG. 9A). The fitting parameters varied significantly along a B-scan (FIG. 9B), showing that segment partitioning helped reduce the effect of variations in local reflectance, allowing a more accurate bulk motion removal.

Figures 10A, 10B, 10C, 10D, 10E:
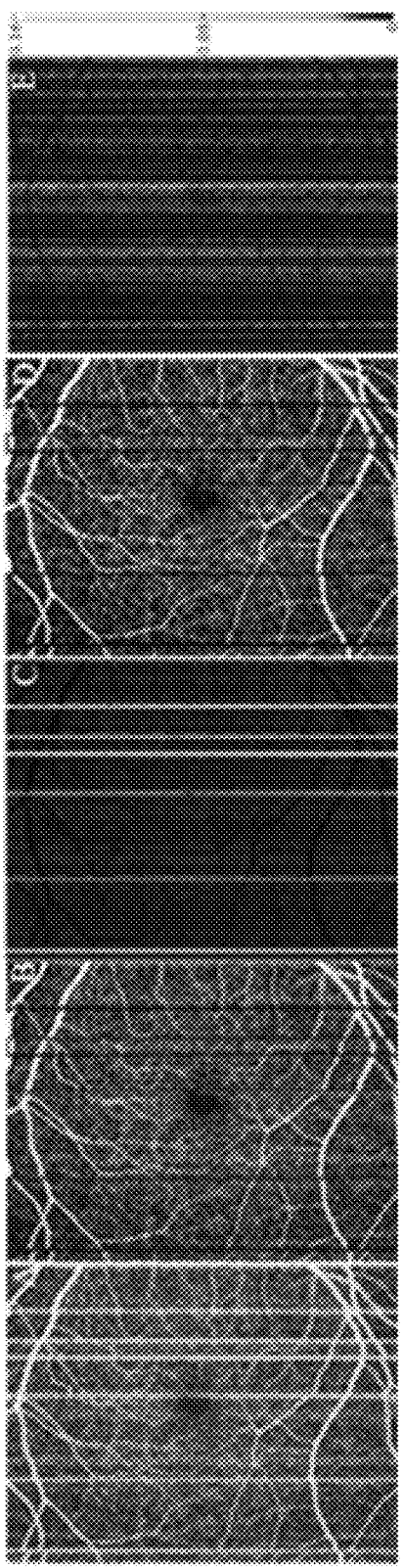
FIGS. 10A-10D demonstrate removal of bulk motion signal from a macular OCTA scan, in accordance with various embodiments.
FIG. 10E illustrates the difference between the angiograms of FIGS. 10B and 10D.
Figure 12A:
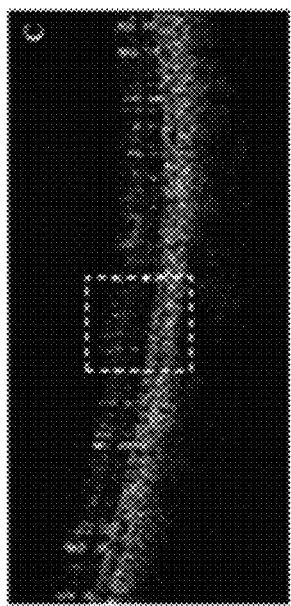
FIGS. 12A-12F demonstrate a qualitative comparison between two bulk motion subtraction algorithms applied to a non-microsaccadic B-frame with large contribution of bulk motion, in accordance with various embodiments. Projection artifacts are not corrected.
Figure 12B:
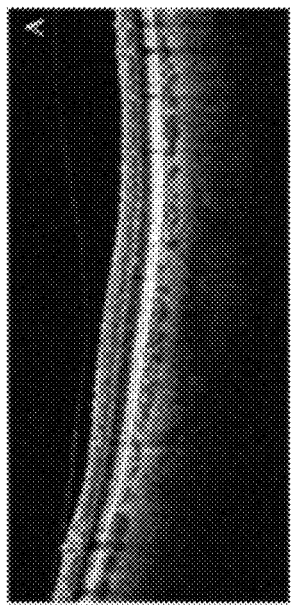
Figure 12C:
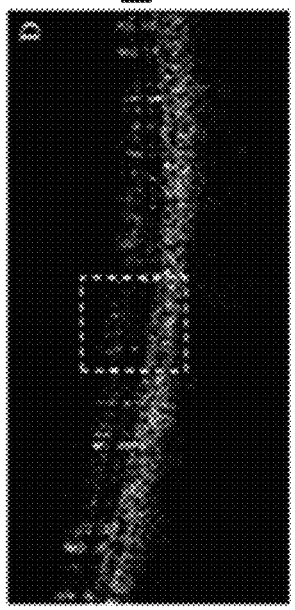
Figure 12D:
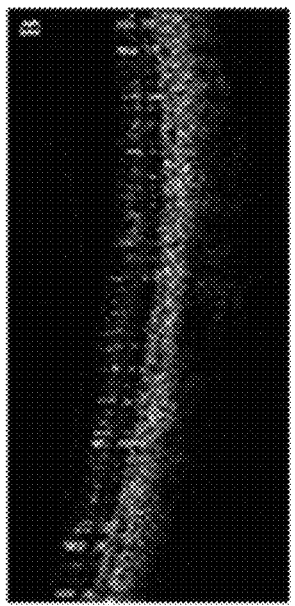
Figure 12E:
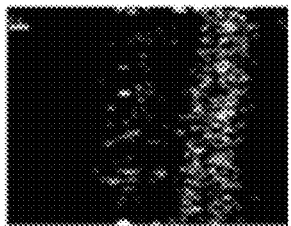
Figure 12F:
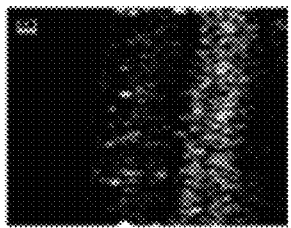

Background signal at FAZ and bulk motion artefactual frames were effectively removed by the thresholding operation (FIGS. 10A-10C), resulting in improved contrast between capillaries and background. Then, the brighter appearance of vascular pixels contained at artefactual lines was corrected by the step of bulk motion velocity subtraction (FIG. 10D). Larger subtraction from vascular voxels occurred in (non-microsaccadic) artefactual frames and smaller subtraction occurred at the flow voxels with decorrelation values near saturation (FIG. 10E).

Compared to the prior median subtraction algorithm (see Table 1), the regression-based bulk motion subtraction algorithm described herein removed a larger percentage of decorrelation noise from the FAZ, achieved a greater improvement in vessel density measurement repeatability, a better signal to noise ratio for flow detection and a better RMS contrast. Two methods preserved similar vascular continuity. No improvement of RMS contrast was observed between median-subtracted and original angiograms (p>0.05), but significant improvement was found after regression-based subtraction. The vessel density did not see significant reduction from the original to the regression-based motion subtracted angiograms (p=0.0687). The median-based algorithm running time was 4.6 seconds while the regression-based algorithm took 20.3 seconds on CPU. A qualitative comparison of the two bulk motion subtraction methods is shown for en face angiograms of the macula and optic disc in FIGS. 11A1-11A7 and 11B1-11B7, and for one representative cross-sectional B-frame in FIGS. 12A-12E.

The bulk motion subtraction algorithm includes, among other features: (1) regression analysis of the background decorrelation vs. reflectance curves, (2) reflectance-dependent thresholding and (3) subtracting bulk motion velocity from the vascular voxels to retrieve bulk motion-free decorrelation values. Both the thresholding operation and the estimation of $v_{BM}$ rely on the accuracy of the linear regression routine, which assumes only background A-lines are selected. If voxels containing real flow signal were mistakenly chosen, they would contribute to larger flow signal at large reflectance voxels, overestimating the slope of the

TABLE 1

Performance Evaluation of Two Bulk Motion Subtraction Methods

| | Percentage of FAZ signal remaining after subtraction | Mean vessel density (coefficient of variation) | Vascular connectivity* | Flow SNR* | RMS contrast* |
|---|---|---|---|---|---|
| Original (No subtraction) | N/A | 87% | 0.920 ± 0.003 | 10.6 ± 1.1 | 0.051 ± 0.002 |
| Median Subtraction | 11.9% + 1.0% | 88% (3.3%) | 0.921 ± 0.0006 | 16.0 ± 1.7 | 0.051 ± 0.002 |
| Regression-based bulk motion subtraction | 9.6% ± 0.8% | 85% | 0.926 ± 0.003 | 19.7 ± 1.8 | 0.060 ± 0.001 |
| p-value** | 0.0034 | 0.0081 | 0.1783 | <0.01 | <0.01 |

*Mean ± standard error.
**Values correspond to the comparison between the two subtraction methods; n = 8.

The pre-compensation performed by inter-B-scan registration could help improve the artifact removal efficiency of the bulk motion subtraction algorithm (See FIG. 13D vs. FIG. 13B). Addition of this step represented an average increase of 9 seconds of raw data processing per frame on CPU. Bright artifacts were not completely removed by inter-B-scan registration alone and a background threshold was still necessary to identify vascular pixels. The pre-compensation could not remove the vessel density dependency on local reflectance by simple thresholding, while the regression-based thresholding proposed in this manuscript provided a correct distribution of vascular pixels. Additionally, the contrast between capillary and background in the resulting image was slightly degraded compared to the case where no displacements are implemented.

Discussion

Previously, correction of bulk motion contribution to flow signal in SSADA was performed by a median subtraction algorithm that underestimates the real bulk motion background and ignores the saturation of decorrelation at vascular voxels. The new regression-based bulk motion subtraction method described herein increases the accuracy of bulk motion subtraction, improving image quality and enhancing the repeatability of vessel density quantification while preserving vascular integrity. This could improve image interpretation by reducing bright line artifacts, and make quantification of vessel density more accurate. Moreover, unlike in the median subtraction algorithm, vascular recognition from background does not require referencing to an avascular region such as the FAZ, allowing computation of the vessel density on scans outside the macula such as the optic nerve head and anterior segment. Although the regression-based bulk motion subtraction algorithm is demonstrated for SSADA, it can be potentially applied to other OCTA implementations such as speckle variance and optical microangiography.

fitting curve. This would cause larger subtracted values, underestimation of the vessel density and degradation of the vascular integrity. In this Example, the first 10 percentile of A-lines with lower flow signal after removing the large vessel mask were chosen, given that the mean vessel density of macular scans did not exceed 90% for healthy subjects. This assumption underestimates the number of flow voxels. In optic disc scans, where some regions have a larger vessel density, the first five percentile of A-lines contained in the whole B-frame were selected. Averaging of voxel values in bins before regression analysis helped to minimize inaccuracies caused by occasional outliers.

Implementation of inter-B-scan registration prior to SSADA alone could not correct the disadvantages inherent to fixed thresholding. On the other hand, implementation of the regression-based algorithm alone was more successful in recognizing vasculature from background and did so in a shorter time. If inter B-scan registration could be optimized to preserve or improve capillary contrast, it can be a supplementary step to further improve the BM removal efficacy.

This algorithm uses information available in a single scan to remove bulk motion background and small-amplitude artifacts. However, given the high prevalence of microsaccadic artifacts in OCTA, it would not eliminate the need for registration of more scans in a clinical scenario. Although commercial systems have adopted various forms of real-time tracking to prevent the recording of microsaccadic motion, drifts between frames before and after microsaccades remain uncorrected, still necessitating registration of at least two volumes for truly artifact-free OCTA.

In summary, this Example demonstrated a method that accurately subtracts bulk motion contribution to decorrelation of background and vascular voxels without affecting vascular integrity. The method recognizes the bulk motion decorrelation dependence on reflectance signal for background voxels; filters out background by a reflectance-dependent thresholding step, subtracts a bulk motion velocity value calculated by a nonlinear model that relates decorrelation and velocity, and finally retrieves the bulk motion-free decorrelation value. The regression-based bulk motion subtraction algorithm improved image quality, vessel density measurement repeatability and accuracy of bulk motion noise removal compared to an earlier median subtraction algorithm. Pre-compensation by OCT inter-B-scan registration before OCTA could improve the efficacy in removing visible artifacts at the cost of increased processing time and reduced capillary-background contrast. The regression-based algorithm takes into account the dependence of decorrelation on reflectance signal and hence, it shows potential to reduce the effect of signal strength on vessel identification. Furthermore, it can be used to identify flow voxels without the need for an avascular reference area. Finally, since it corrects flow signal on voxels of the three-dimensional OCTA data set, it might improve capillary flow index quantification accuracy and image quality on projection-resolved OCTA.

Example 2

OCT Angiography Image Processing System for Bulk Motion Removal

Figure 14:
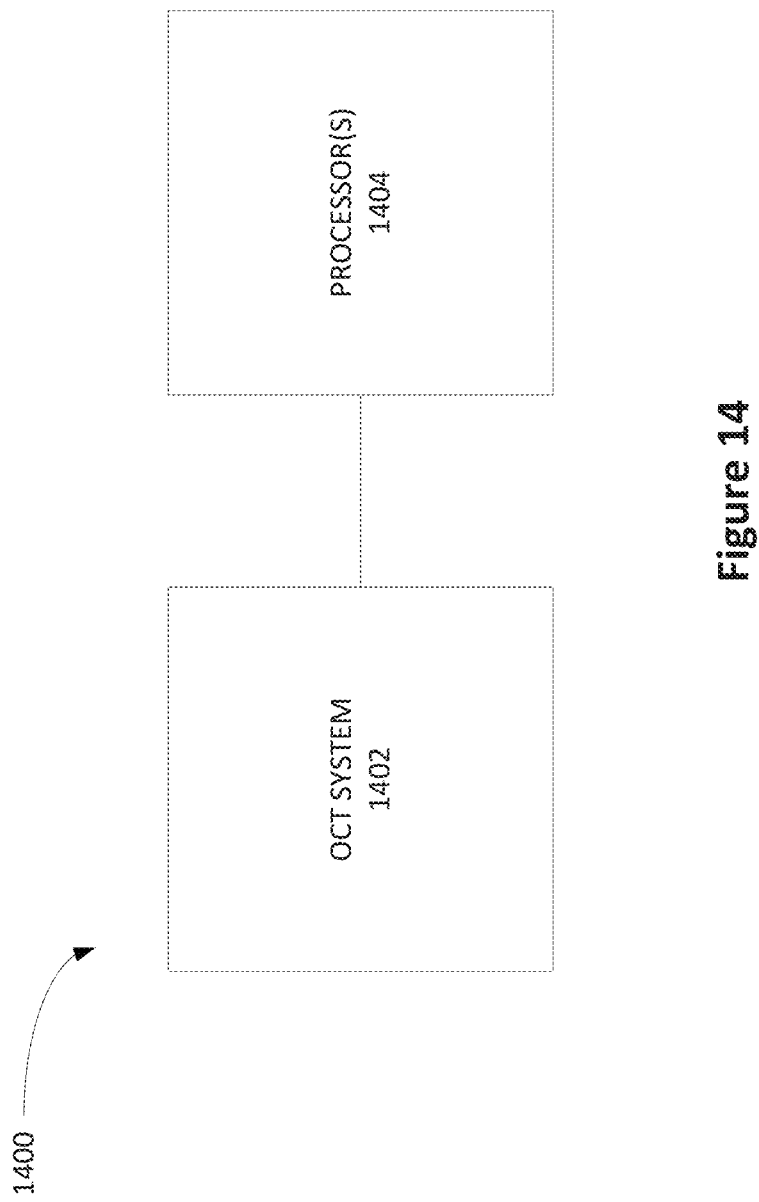
FIG. 14 schematically shows an example system for processing OCT datasets to remove bulk motion in accordance with the disclosure.

FIG. 14 schematically shows an example system 1400 for OCT angiography image processing in accordance with various embodiments. System 1400 comprises an OCT system 1402 configured to acquire an OCT image comprising OCT interferograms and one or more processors or computing systems 1404 that are configured to implement the various processing routines described herein. OCT system 1400 may comprise an OCT system suitable for OCT angiography applications, e.g., a swept source OCT system or spectral domain OCT system.

In various embodiments, an OCT system may be adapted to allow an operator o perform various tasks. For example, an OCT system may be adapted to allow an operator to configure and/or launch various ones of the herein described methods. In some embodiments, an OCT system may be adapted to generate, or cause to be generated, reports of various information including, for example, reports of the results of scans run on a sample.

In embodiments of OCT systems comprising a display device, data and/or other information may be displayed for an operator. In embodiments, a display device may be adapted to receive an input (e.g., by a touch screen, actuation of an icon, manipulation of an input device such as a joystick or knob, etc.) and the input may, in some cases, be communicated (actively and/or passively) to one or more processors. In various embodiments, data and/or information may be displayed, and an operator may input information in response thereto.

In some embodiments, the above described methods and processes may be tied to a computing system, including one or more computers. In particular, the methods and processes described herein may be implemented as a computer application, computer service, computer API, computer library, and/or other computer program product.

Figure 15:
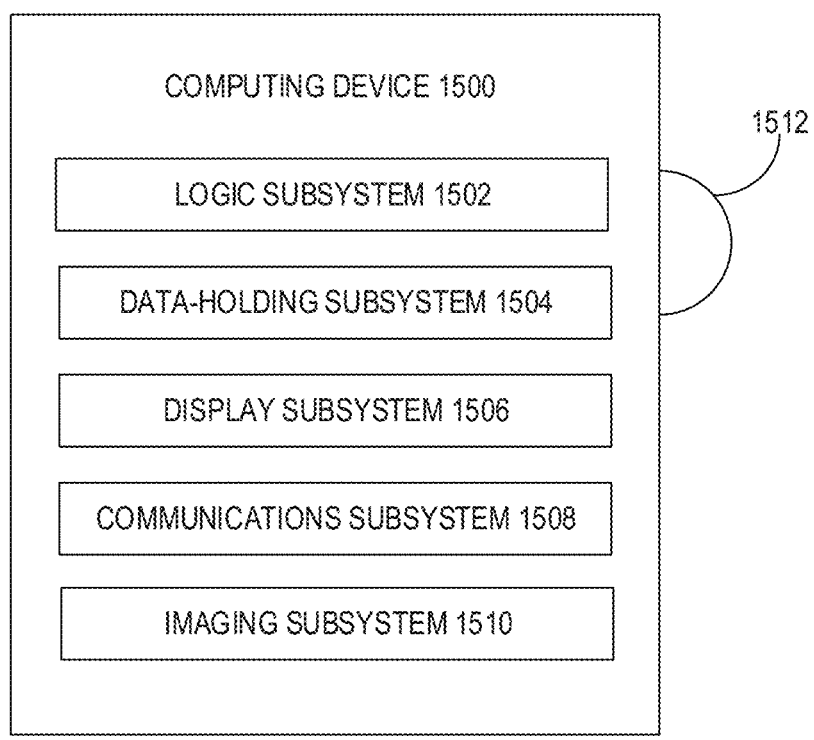
FIG. 15 schematically shows an example of a computing system in accordance with the disclosure.

FIG. 15 schematically shows a non-limiting computing device 1500 that may perform one or more of the methods and/or processes described herein. For example, computing device 1500 may represent a processor included in system 1400 described above, and may be operatively coupled to, in communication with, or included in an OCT system or OCT image acquisition apparatus. Computing device 1500 is shown in simplified form. It is to be understood that virtually any computer architecture may be used without departing from the scope of this disclosure. In different embodiments, computing device 1500 may take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1500 includes a logic subsystem 1502 and a data-holding subsystem 1504. Computing device 1500 may optionally include a display subsystem 1506, a communication subsystem 1508, an imaging subsystem 1510, and/or other components not shown in FIG. 15. Computing device 1500 may also optionally include user input devices such as manually actuated buttons, switches, keyboards, mice, game controllers, cameras, microphones, and/or touch screens, for example.

Logic subsystem 1502 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. For example, the one or more processors may comprise physical circuitry programmed to perform various acts described herein. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 1504 may include one or more physical, non-transitory, devices configured to hold data and/or instructions executable by the logic subsystem to implement the herein described methods and processes. When such methods and processes are implemented, the state of data-holding subsystem 1504 may be transformed (e.g., to hold different data).

Data-holding subsystem 1504 may include removable media and/or built-in devices. Data-holding subsystem 1504 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1504 may include devices with one or more of the following characteristics: volatile, nonvolatile, dynamic, static, read/write, read-only, random access, sequential access, location addressable, file addressable, and content addressable. In some embodiments, logic subsystem 1502 and data-holding subsystem 1504 may be integrated into one or more common devices, such as an application specific integrated circuit or a system on a chip.

FIG. 15 also shows an aspect of the data-holding subsystem in the form of removable computer-readable storage media 1512, which may be used to store and/or transfer data and/or instructions executable to implement the herein described methods and processes. Removable computer-readable storage media 1512 may take the form of CDs, DVDs, HD-DVDs, Blu-Ray Discs, EEPROMs, flash memory cards, USB storage devices, and/or floppy disks, among others.

When included, display subsystem 1506 may be used to present a visual representation of data held by data-holding subsystem 1504. As the herein described methods and processes change the data held by the data-holding subsystem, and thus transform the state of the data-holding subsystem, the state of display subsystem 1506 may likewise be transformed to visually represent changes in the underlying data. Display subsystem 1506 may include one or more display devices utilizing virtually any type of technology. Such display devices may be combined with logic subsystem 1502 and/or data-holding subsystem 1504 in a shared enclosure, or such display devices may be peripheral display devices.

When included, communication subsystem 1508 may be configured to communicatively couple computing device 1500 with one or more other computing devices. Communication subsystem 1508 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 1500 to send and/or receive messages to and/or from other devices via a network such as the Internet.

When included, imaging subsystem 1510 may be used acquire and/or process any suitable image data from various sensors or imaging devices in communication with computing device 1500. For example, imaging subsystem 1510 may be configured to acquire OCT image data, e.g., interferograms, as part of an OCT system, e.g., OCT system 1402 described above. Imaging subsystem 1510 may be combined with logic subsystem 1502 and/or data-holding subsystem 1504 in a shared enclosure, or such imaging subsystems may comprise periphery imaging devices. Data received from the imaging subsystem may be held by data-holding subsystem 1504 and/or removable computer-readable storage media 1512, for example.

Appended to this description are some additional documents that include additional description and figures of various embodiments. These documents form a part of the present disclosure.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

What is claimed is:

1. A method comprising:
   obtaining an optical coherence tomography (OCT) dataset for a sample, the OCT dataset including reflectance values;
   obtaining an OCT angiography (OCTA) dataset for the sample, the OCTA dataset including decorrelation values corresponding to a plurality of OCTA B-scans;
   determining a bulk motion decorrelation threshold associated with individual OCTA B-scans of the plurality of OCTA B-scans based on a linear regression of a subset of the decorrelation values of the respective individual OCTA B-scan with a logarithm of the corresponding reflectance values;
   setting decorrelation values of the OCTA dataset having decorrelation values that are lower than the corresponding bulk motion decorrelation threshold to zero to obtain a thresholded OCTA dataset; and
   generating a flow image from the thresholded OCTA dataset.

2. The method of claim 1, further comprising:
   assigning the decorrelation values of the subset of the decorrelation values and the logarithm of the corresponding reflectance values to bins based on the reflectance values;
   averaging the natural logarithm of the reflectance values within each bin to obtain respective average log reflectance values; and
   averaging the decorrelation values within each bin to obtain respective average decorrelation values;
   wherein the linear regression is performed on the average log reflectance values and the average decorrelation values.

3. The method of claim 2, wherein the linear regression is a first linear regression, wherein the method further comprises performing a second linear regression using a fitting slope of the first linear regression and root-mean-square (RMS) deviation values corresponding to a deviation of the decorrelation values, and wherein the bulk motion decorrelation threshold is determined based on the first and second linear regressions.

4. The method of claim 1, wherein the estimated bulk motion is in a decorrelation domain, and wherein the generating the flow image based on the vascular OCTA dataset includes:
   determining a bulk motion velocity voxels of the thresholded OCTA dataset based on the determined bulk motion decorrelation threshold and a saturation value;
   determining a velocity value for individual voxels of the thresholded OCTA dataset based on the respective decorrelation values;
   subtracting the bulk motion velocity from the respective velocity values for the individual voxels to obtain respective corrected velocity values; and
   obtaining corrected decorrelation values based on the corrected velocity values;
   wherein the flow image is generated from the corrected decorrelation values.

5. The method of claim 1, wherein the subset of the reflectance values corresponds to non-vascular A-scans of the individual OCTA B-scan.

6. The method of claim 5, further comprising identifying the non-vascular A-scans as a pre-determined percentage of the A-scans having a lowest maximum decorrelation value among all or a selected group of the A-scans.

7. The method of claim 1, wherein the flow image is an en face OCT angiogram.

8. The method of any one of claims 1 to 7, further comprising dividing individual OCTA B-scans of the plurality of OCTA B-scans into a plurality of segments along a transverse dimension, wherein the bulk motion decorrelation threshold is determined for individual segments of the plurality of segments.

9. A method comprising:
obtaining an optical coherence tomography (OCT) dataset for a sample, the OCT dataset including reflectance values;
obtaining an OCT angiography (OCTA) dataset for the sample, the OCTA dataset including decorrelation values corresponding to a plurality of OCTA B-scans;
dividing individual OCTA B-scans of the plurality of OCTA B-scans into segments along a transverse dimension;
estimating bulk motion within each segment of the individual OCTA B-scans based on non-vascular A-scans within the respective segment and the corresponding reflectance values of the OCT dataset; and
generating a flow image from the OCTA dataset and the estimated bulk motion.

10. The method of claim 9, further comprising identifying the non-vascular A-scans within the respective segment as a pre-determined percentage of the A-scans having a lowest maximum decorrelation value among all or a selected group of A-scans of the segment.

11. The method of claim 9, wherein the estimating bulk motion includes performing a linear regression of the decorrelation values associated with the non-vascular A-scans with a logarithm of the corresponding reflectance values.

12. The method of claim 11, further comprising:
assigning the decorrelation values associated with the non-vascular A-scans and the logarithm of the corresponding reflectance values and the corresponding decorrelation values to bins based on the reflectance values;
averaging the logarithm of the reflectance values within each bin to obtain respective average log reflectance values; and
averaging the decorrelation values within each bin to obtain respective average decorrelation values;
wherein the linear regression is performed on the average log reflectance values and the average decorrelation values.

13. The method of claim 12, wherein the linear regression is a first linear regression, and wherein the method further comprises performing a second linear regression using a fitting slope of the first linear regression and root-mean-square (RMS) deviation values corresponding to a deviation of the decorrelation values; and
wherein the estimating bulk motion includes determining a bulk motion decorrelation threshold based on the first and second linear regressions.

14. The method of claim 13, wherein the generating the flow image includes:
setting voxels of the OCTA dataset having decorrelation values that are lower than the corresponding bulk motion decorrelation threshold to zero to obtain a thresholded OCTA dataset; and
generating the flow image based on the thresholded OCTA dataset.

15. The method of claim 14, wherein the estimated bulk motion is in a decorrelation domain, and wherein the generating the flow image based on the vascular OCTA dataset includes:

determining a bulk motion velocity for the respective segment based on the respective estimated bulk motion and a saturation value;
determining a velocity value for individual voxels of the thresholded OCTA dataset based on the respective decorrelation values;
subtracting the bulk motion velocity from the respective velocity values for the individual voxels to obtain respective corrected velocity values; and
obtaining corrected decorrelation values based on the corrected velocity values;
wherein the flow image is generated from the corrected decorrelation values.

16. The method of claim 9, wherein the flow image is an en face OCT angiogram.

17. A system for removing bulk motion from an optical coherence tomography (OCT) angiogram, the system comprising:
an OCT system configured to acquire an OCT dataset and an OCT angiography dataset for a sample, the OCT dataset including reflectance values, and the OCTA dataset including decorrelation values corresponding to a plurality of OCTA B-scans;
a logic subsystem; and
a data holding subsystem comprising machine-readable instructions stored thereon that are executable by the logic subsystem to:
perform a linear regression of a subset of the decorrelation values of respective individual OCTA B-scans of the plurality of OCTA B-scans with a logarithm of the corresponding reflectance values;
determine a bulk motion decorrelation threshold associated with the individual OCTA B-scans based on the linear regression;
set decorrelation values of the OCTA dataset having decorrelation values that are lower than the corresponding bulk motion decorrelation threshold to zero to obtain a thresholded OCTA dataset; and
generate a bulk-motion subtracted flow image based on the thresholded OCTA dataset.

18. The system of claim 17, wherein the instructions are further executable by the logic subsystem to:
assign the decorrelation values of the subset of decorrelation values and the corresponding reflectance values to bins based on the reflectance values;
average the logarithm of the reflectance values within each bin to obtain respective average log reflectance values; and
average the decorrelation values within each bin to obtain respective average decorrelation values;
wherein the linear regression is performed on the average log reflectance values and the average decorrelation values.

19. The system of claim 18, wherein the linear regression is a first linear regression, wherein the instructions are further executable by the logic subsystem to perform a second linear regression using a fitting slope of the first linear regression and root-mean-square (RMS) deviation values corresponding to a deviation of the decorrelation values, and wherein the bulk motion decorrelation threshold is determined based on the first and second linear regressions.

20. The system of claim 17, wherein the estimated bulk motion is in a decorrelation domain, and wherein, to generate the flow image based on the vascular OCTA dataset, the logic subsystem is to:

determine a bulk motion velocity for voxels of the thresholded OCTA dataset based on the determined bulk motion decorrelation threshold and a saturation value;

determine a velocity value for individual voxels of the thresholded OCTA dataset based on the respective decorrelation values;

subtract the bulk motion velocity from the respective velocity values for the individual voxels to obtain respective corrected velocity values;

obtain corrected decorrelation values based on the corrected velocity values; and generated the flow image from the corrected decorrelation values.

21. The system of claim 17, wherein the subset of the decorrelation values corresponds to non-vascular A-scans of the individual OCTA B-scan.

22. The system of claim 21, wherein the instructions are further executable by the logic subsystem to identify the non-vascular A-lines as a pre-determined percentage of the A-scans having a lowest maximum decorrelation value among all or a selected group of the A-scans.

23. The system of claim 17, wherein the flow image is an en face OCT angiogram.

24. The system of claim 17, wherein the instructions are further executable by the logic subsystem to divide the individual OCTA B-scans into a plurality of segments along a transverse dimension, wherein the bulk motion decorrelation threshold is determined for individual segments of the plurality of segments.

* * * * *

UNITED STATES PATENT AND TRADEMARK OFFICE
CERTIFICATE OF CORRECTION

PATENT NO. : 10,588,572 B2
APPLICATION NO. : 15/805392
DATED : March 17, 2020
INVENTOR(S) : Yali Jia et al.

It is certified that error appears in the above-identified patent and that said Letters Patent is hereby corrected as shown below:

In the Specification

At Column 1, Lines 19-22, under the heading ACKNOWLEDGEMENT OF GOVERNMENT SUPPORT, please delete the following:
"This invention was made with government support under EY023285, EY018184, EY024544, and DK104397 awarded by the National Institutes of Health. The Government has certain rights in the invention."
And replace it with the following:
--This invention was made with government support under R01 EY023285, R01 EY018184, R01 EY024544, R01 EY027833, and R01 EY028755 awarded by the National Institutes of Health. The government has certain rights in the invention--

Signed and Sealed this
Twenty-sixth Day of September, 2023

Katherine Kelly Vidal
*Director of the United States Patent and Trademark Office*